US011154680B2

(12) United States Patent
Walls et al.

(10) Patent No.: US 11,154,680 B2
(45) Date of Patent: Oct. 26, 2021

(54) HEADGEAR FOR A RESPIRATORY MASK

(71) Applicant: Fisher & Paykel Healthcare Limited, Auckland (NZ)

(72) Inventors: Bruce Michael Walls, Auckland (NZ); Matthew Roger Stephenson, Auckland (NZ); Jeremy Owen Young, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 476 days.

(21) Appl. No.: 15/511,213

(22) PCT Filed: Sep. 16, 2015

(86) PCT No.: PCT/NZ2015/050148
§ 371 (c)(1),
(2) Date: Mar. 14, 2017

(87) PCT Pub. No.: WO2016/043602
PCT Pub. Date: Mar. 24, 2016

(65) Prior Publication Data
US 2017/0281894 A1    Oct. 5, 2017

Related U.S. Application Data

(60) Provisional application No. 62/050,911, filed on Sep. 16, 2014.

(51) Int. Cl.
*A61M 16/06* (2006.01)
(52) U.S. Cl.
CPC ......... *A61M 16/0683* (2013.01); *A61M 16/06* (2013.01); *A61M 2210/0618* (2013.01)
(58) Field of Classification Search
CPC .............. A61M 16/06; A61M 16/0605; A61M 16/0683; A61M 16/0694;
(Continued)

(56) References Cited

U.S. PATENT DOCUMENTS 4,422,456 A  12/1983  Tiep
5,653,228 A *  8/1997  Byrd ................. A61M 16/0488
128/207.11
(Continued)

FOREIGN PATENT DOCUMENTS

AU  2013206439  7/2013
AU  2013257426  11/2013
(Continued)

OTHER PUBLICATIONS

Screen captures from YouTube video clip entitled "YKK Rotary Center Release Buckle," 1 page, uploaded on Jan. 2, 2014 by user "Sailrite". Retrieved from Internet: <https://www.youtube.com/watch?v=j-AM-vc2Qpl>. (Year: 2014).*
(Continued)

*Primary Examiner* — Bradley H Philips
*Assistant Examiner* — Savannah L Gabriel
(74) *Attorney, Agent, or Firm* — Knobbe, Martens, Olson & Bear, LLP

(57) ABSTRACT

A headgear for a respiratory mask has first and second straps configured to be connected to each other by first and second buckles. The straps are configured to overlap in a region that contacts the rear of a user's head. The overlapping regions of the first and second straps can be positioned in a bifurcated configuration to improve stability on a user's head. The first and second buckles can feature a glider end through which one of the first and second straps can slide and a strap attachment end to which the other strap is permanently connected. In some embodiments, the first and second buckles have two components that are pivotally connected to allow adjustment of the headgear size whilst in a bifurcated configuration.

19 Claims, 18 Drawing Sheets

(58) Field of Classification Search
CPC ....... A61M 2210/0618; A44B 11/2553; A44B 11/2557; A44B 11/258; A44B 11/2588
See application file for complete search history.

(56) References Cited

U.S. PATENT DOCUMENTS

| | | | |
|---|---|---|---|
| 8,356,895 B2* | 1/2013 | Jackson | A61F 9/023 351/159.01 |
| 2003/0196658 A1 | 10/2003 | Ging et al. | |
| 2005/0204456 A1 | 9/2005 | Piper et al. | |
| 2006/0283461 A1* | 12/2006 | Lubke | A61M 16/06 128/207.11 |
| 2007/0125385 A1 | 6/2007 | Ho et al. | |
| 2008/0236589 A1 | 10/2008 | Bronson | |
| 2008/0301916 A1* | 12/2008 | Lundh | A44B 11/258 24/568 |
| 2009/0183739 A1 | 7/2009 | Wondka | |
| 2010/0258132 A1 | 10/2010 | Moore | |
| 2011/0146685 A1 | 6/2011 | Allan et al. | |
| 2013/0277405 A1* | 10/2013 | Jensen | A45C 13/30 224/600 |
| 2014/0026890 A1* | 1/2014 | Haskard | A61M 16/0666 128/207.11 |
| 2014/0246025 A1 | 9/2014 | Wondka | |
| 2015/0246200 A1* | 9/2015 | Neff, Jr. | A61M 16/0816 128/202.27 |
| 2018/0236276 A1* | 8/2018 | Moon | A41D 13/1161 |

FOREIGN PATENT DOCUMENTS

| | | |
|---|---|---|
| AU | 2014201197 | 3/2014 |
| AU | 2014201200 | 3/2014 |
| EP | 1293227 | 3/2003 |
| EP | 2022528 | 2/2009 |
| EP | 2130563 | 12/2009 |
| EP | 2140902 | 1/2010 |
| EP | 2145645 | 1/2010 |
| EP | 2529781 | 12/2012 |
| EP | 2679266 | 1/2014 |
| WO | WO 2004/012803 | 2/2004 |
| WO | WO 2004/073777 | 9/2004 |
| WO | WO 2005/018523 | 3/2005 |
| WO | WO 2007/006089 | 1/2007 |
| WO | WO 2007/08180 | 7/2007 |
| WO | WO 2008/070929 | 6/2008 |
| WO | WO 2009/052560 | 4/2009 |
| WO | WO 2009/059353 | 5/2009 |
| WO | WO 2009/108994 | 9/2009 |
| WO | WO 2009/108995 | 9/2009 |
| WO | WO 2009/109005 | 9/2009 |
| WO | WO 2009/139647 | 11/2009 |
| WO | WO 2010/066004 | 6/2010 |
| WO | WO 2010/139014 | 12/2010 |
| WO | WO 2011/110962 | 9/2011 |
| WO | WO 2012/177152 | 11/2012 |
| WO | WO 2012/167327 | 12/2012 |
| WO | WO 2013/026091 | 2/2013 |
| WO | WO 2013/076622 | 5/2013 |
| WO | WO 2014/077708 | 5/2014 |
| WO | WO 2014/110626 | 7/2014 |
| WO | WO 2014/142681 | 9/2014 |
| WO | WO 2014/174393 | 10/2014 |
| WO | WO 2014/175752 | 10/2014 |
| WO | WO 2014/182179 | 11/2014 |
| WO | WO 2015/020540 | 2/2015 |

OTHER PUBLICATIONS

International Search Report, PCT/NX2015/050148, dated Dec. 17, 2015, in 40 pages.
Australian Government, Examination Report No. 1, Application No. PCT/NZ2015/050148, dated Jun. 6, 2019 in 4 pages.

* cited by examiner

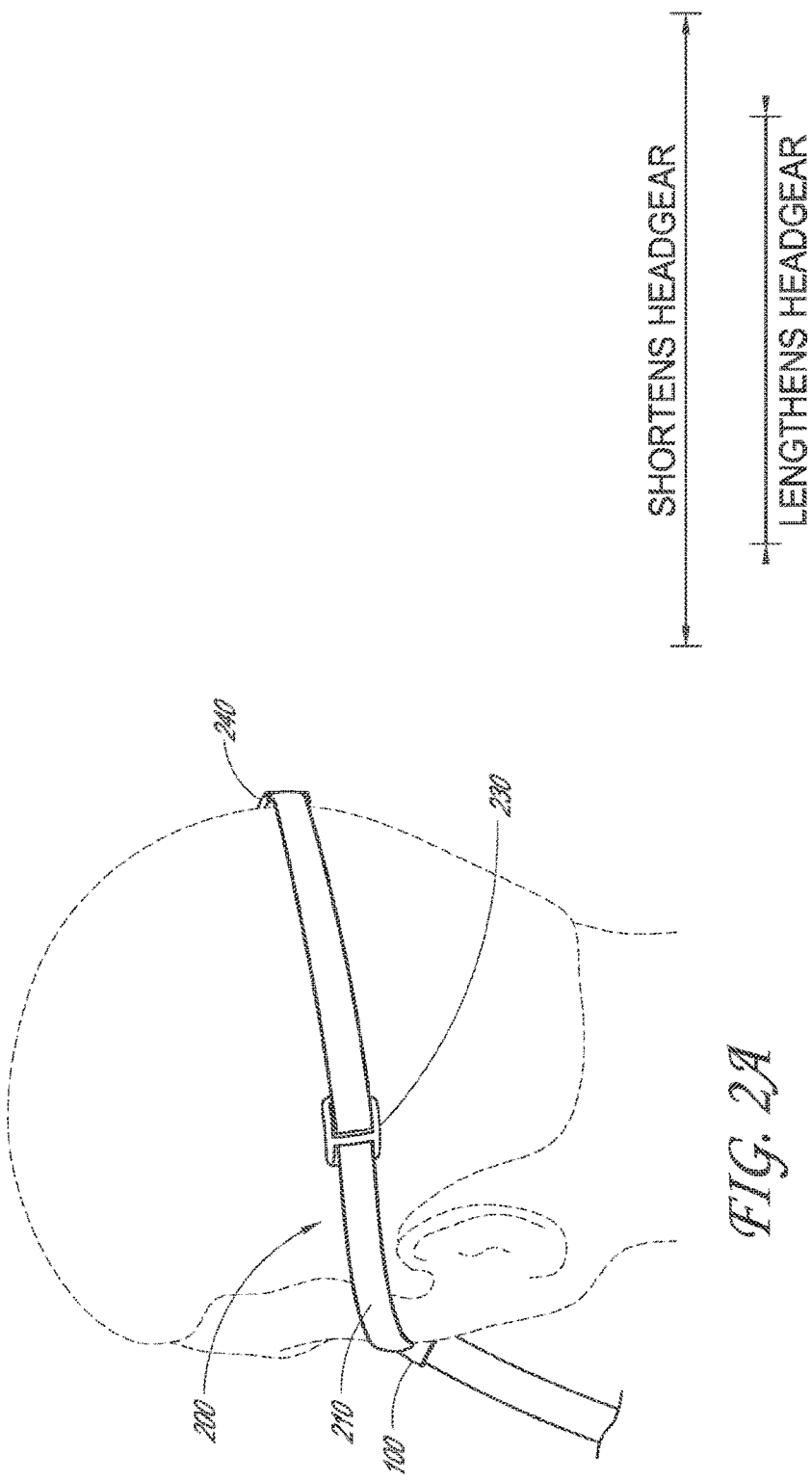
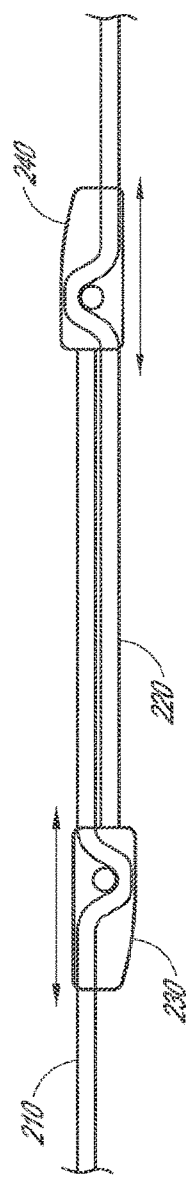
FIG. 2A
FIG. 2B

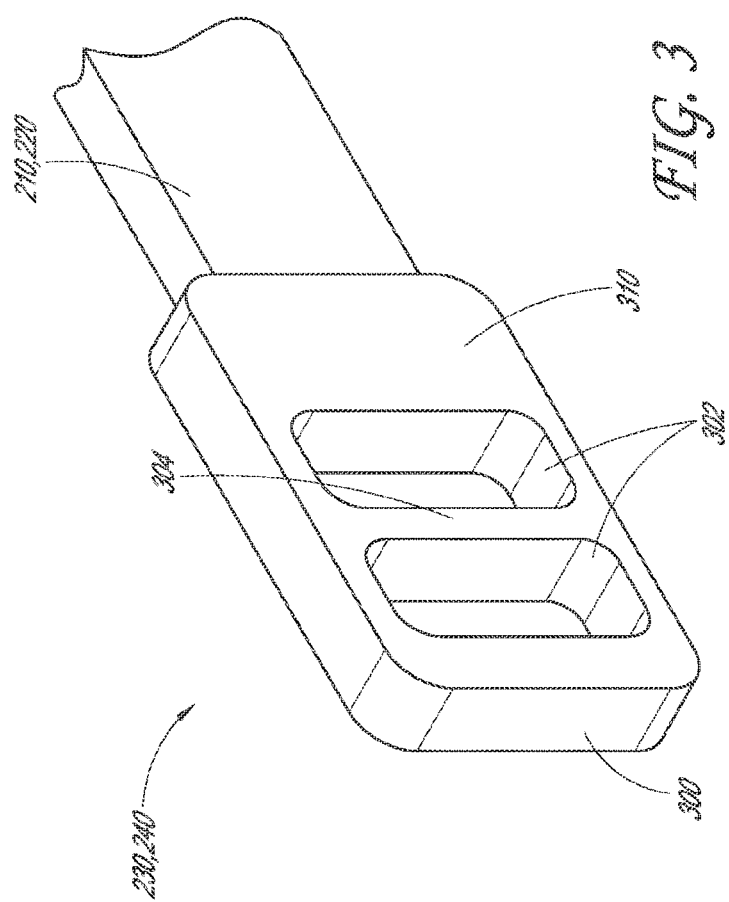

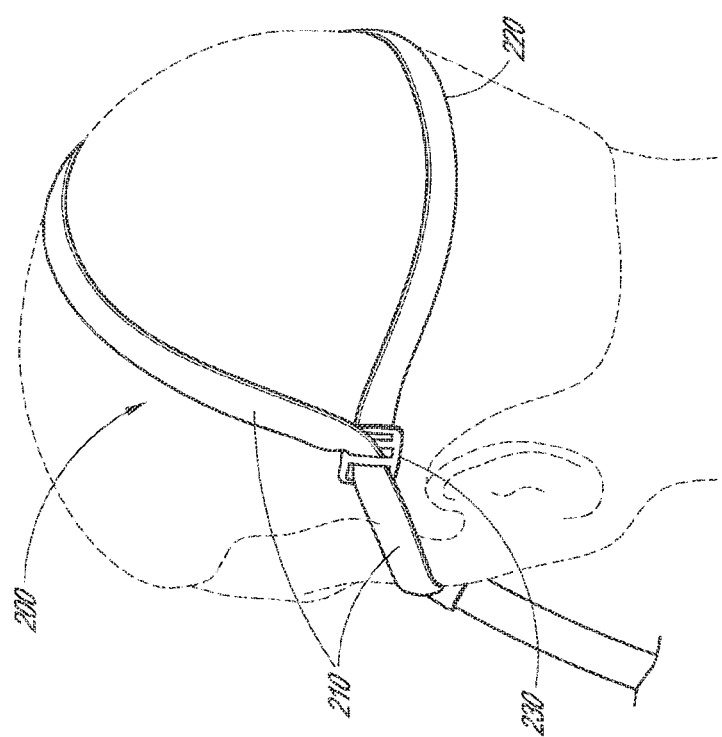

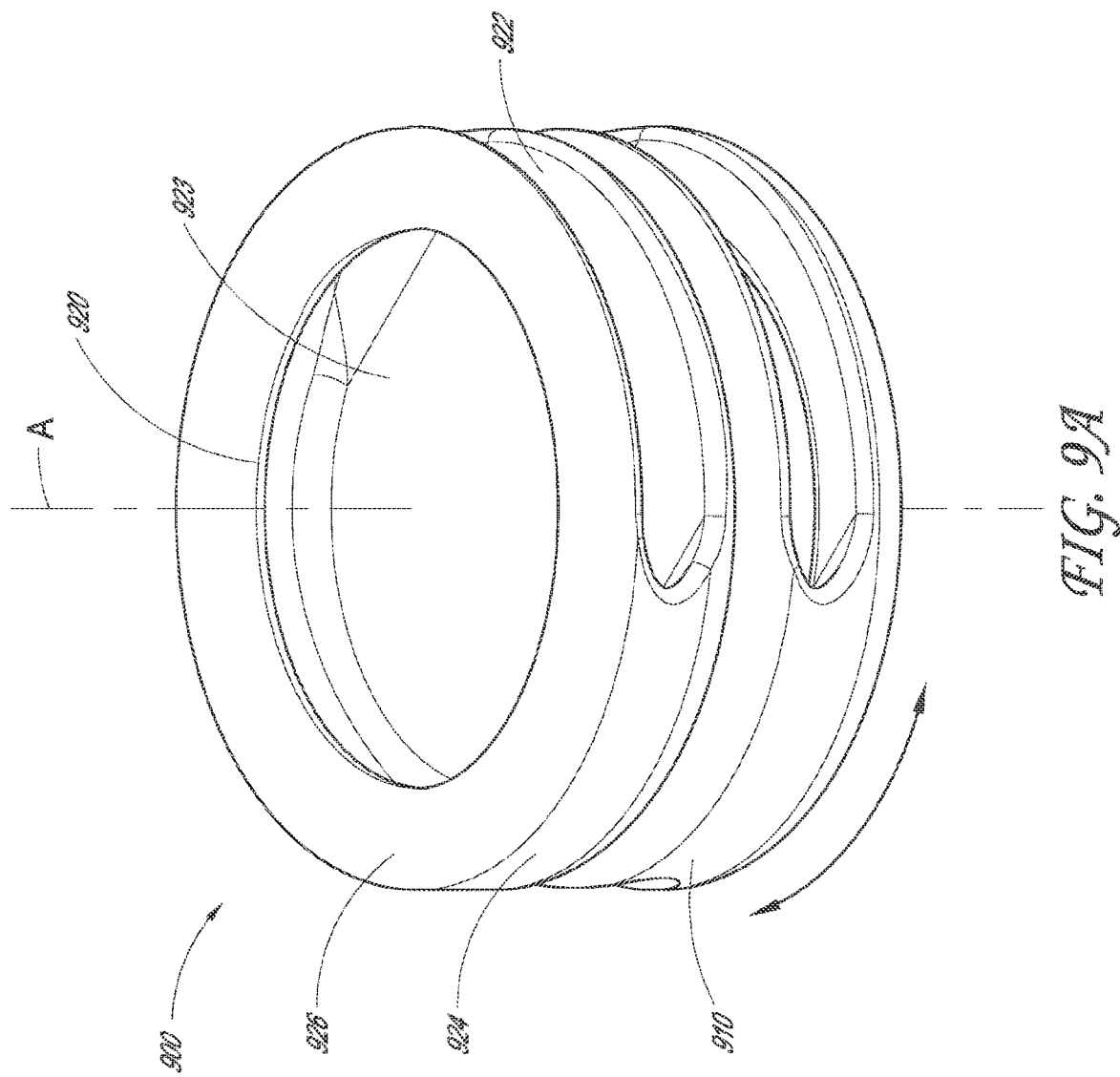

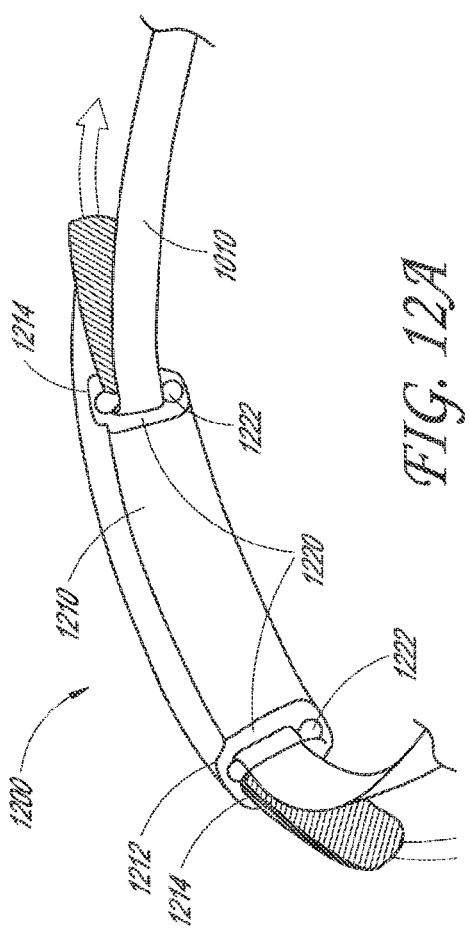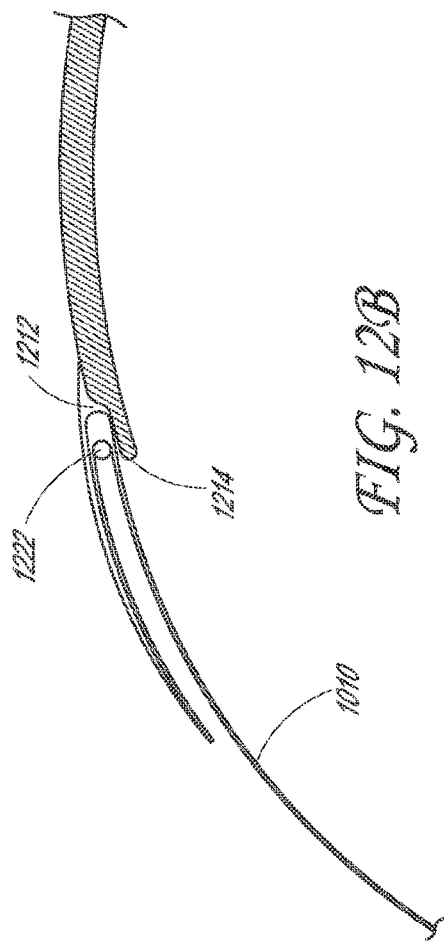

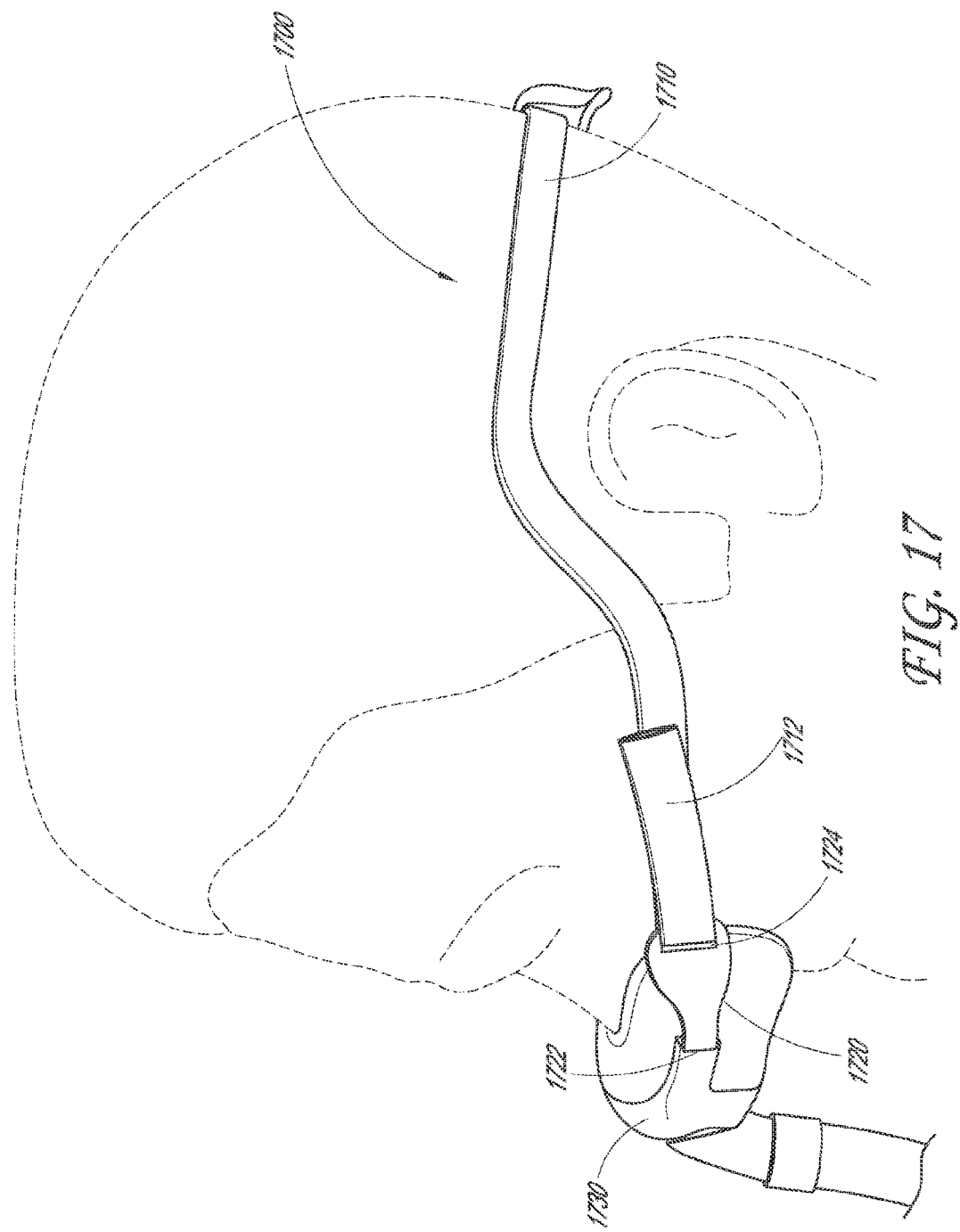

HEADGEAR FOR A RESPIRATORY MASK

INCORPORATION BY REFERENCE TO ANY PRIORITY APPLICATIONS

Any and all applications for which a foreign or domestic priority claim is identified in connection with the present application are hereby incorporated by reference herein and made a part of the present disclosure. The present application is a national phase of PCT Application No. PCT/NZ2015/050148, which claims the priority benefit of U.S. Provisional Application No. 62/050,911, filed Sep. 16, 2014, the entirety of which is hereby incorporated by reference herein.

BACKGROUND

Technical Field

The present disclosure generally relates to a headgear for a respiratory mask. More particularly, the present disclosure relates to headgear having a configuration that can be similar to a single strap configuration that is adjustable and configured to be stable on a user's head.

Description of the Related Art

The treatment of respiratory ailments or conditions with therapies, such as Non-Invasive Ventilation (NIV), Bi-level or Continuous Positive Airway Pressure (CPAP), involves the delivery of pressurized air to the airways of a human via a conduit and a breathing apparatus (e.g., a respiratory mask or cannula). Typically, respiratory masks are configured as nasal, pillows, full face, or oral interfaces that create at least a substantial "seal" in or around the nose and/or the mouth of a user.

A result of the respiratory mask creating this "seal" is that the combination of the enclosure area of the respiratory mask and its internal pressure creates a resulting force that attempts to push the mask off of the user's face. To counteract this force, it is normal to use a headgear comprising a series of straps that pass around the back and/or the top of a user's head. As shown in FIG. 1, for a relatively small respiratory mask 100, such as a nasal or pillows mask, which only "seals" in or around the nose of a user, a headgear 110 comprising a single elastic strap can be sufficient to counteract the resulting force and to retain the mask 100 on a user's face. This single elastic strap configuration has the benefits of being low profile and unobtrusive for the user to wear and of making donning and doffing of the respiratory mask 100 quick and easy.

A headgear comprising a single elastic strap may, however, not be as stable on the user's head as a headgear comprising multiple straps and such a headgear does not provide users with as much ability to adjust the fit of the headgear to suit their individual requirements. Single straps are more prone to slipping on the back of a user's head during use, which may result in the respiratory mask being displaced and the "seal" being broken.

BRIEF SUMMARY

Certain aspects of the present disclosure relate to a headgear for a respiratory mask, which is improved in at least one or more respects or at least provides users with a useful choice.

In accordance with certain embodiments disclosed herein, a headgear can comprise a first strap, a second strap, and a pair of buckles. The pair of buckles can comprise a corresponding buckle for the first and second straps. Each corresponding buckle can comprise a glider portion, a strap attachment portion, and a pivot connection between the glider portion and the strap attachment portion. Each of the first and second straps can comprise a first end, a second end, and a length therebetween. Each of the first and second straps can be configured to connect to the respiratory mask at the first end, to adjustably couple to the corresponding buckle at the glider portion, and to be fixedly coupled to the strap attachment portion of an other buckle of the pair of buckles at the second end. Each buckle can be configured to move along the length of the first or second strap to adjust the size of the headgear.

In various embodiments, the first or second strap can comprise fabric. The first or second strap can comprise a tubular structure. The first or second strap can comprise elastic or inelastic material. For at least one buckle, the glider portion can include at least one aperture through which the first or second strap passes. In some embodiments, for at least one buckle, the glider portion or the strap portion can comprise a circular profile. In some such embodiments, the glider portion and the strap attachment portion can comprise a circular profile and can overlap such that the buckle forms a single circular profile. In some embodiments, for at least one buckle, the glider portion and the strap attachment portion can comprise a semi-circular profile on one end and a rectangular profile on another end. In some such embodiments, the pivot connection can be located at the semi-circular profile ends of the glider portion and the strap attachment portion. For example, the semi-circular profile ends can overlap.

In some embodiments, at least one of the first and second straps can be overmoulded to the strap attachment portion of the other buckle, or at least one of the first and second straps can be welded to the strap attachment portion of the other buckle. For at least one buckle, the pivot connection can comprise a snap-fit dome and a ring.

In various embodiments, the headgear can be configured to be adapted between a first configuration and a second configuration. The first configuration can comprise portions of the first and second straps overlapping in a region between the pair of buckles. The second configuration can comprise the portions of the first and second straps bifurcating in the region of the pair of buckles. In some embodiments, the pair of buckles can be configured to adjust the size of the headgear while in the second configuration.

For example, an embodiment of the headgear disclosed herein comprises first and second straps configured to be connected to each other by first and second buckles, wherein the straps are configured to overlap in a region that contacts a rear of a user's head, in use. In use, the first and second straps of the headgear can be arranged in a bifurcated configuration to improve stability on the user's head.

The first and second buckles can comprise a glider end or half through which one of the first and second straps can slide through and a strap attachment end or fixed strap half to which the other strap can be permanently connected. In some embodiments, the first and second buckles comprise two components that are pivotally connected. This may allow the size of the headgear to be adjusted whilst in a bifurcated configuration.

In accordance with certain embodiments disclosed herein, a headgear can comprise a first strap, a second strap, and a linking member between the first and second straps. Each of the first and second straps can comprise a mask connection portion, an adjustment portion, and a length therebetween. The linking member can comprise a first end and a second end. The linking member can be coupled to the adjustment portion of the first strap via a first buckle at the first end and coupled to the adjustment portion of be second strap via a second buckle at the second end.

In various embodiments, the first or second strap can comprise fabric. At least one of the first and second straps can comprise a tubular structure. At least one of the first and second straps can comprise a semi-rigid substrate, and the tubular structure can be configured to move over the semi-rigid substrate at a corresponding mask connection portion. At least one of the first and second straps can comprise a hook and loop fastener configured to set the length of the first or second strap.

In some embodiments, the linking member can comprise a label. In some examples, the linking member can comprise a fabric strap. The linking member can also comprise a overmoulded or printed grip. The linking member can comprise a plastic component. The linking member of various embodiments can comprise a degree of flexibility configured to allow the linking member to conform to a user's head.

In some embodiments, the first or second buckle can be a separate component from the linking member. The first or second buckle can be welded to the linking member. In some other embodiments, the first or second buckle can be integrally formed with the linking member. In various embodiments, the length of the first and second straps can be adjusted by pulling the adjustment portions of the first and second straps.

As another example, another embodiment of the headgear disclosed herein comprises a label with integrated buckles, wherein the buckles provide a mechanism to adjust the length of two attached side straps and, thus, the size of the headgear. The label comprises an elongate textile or plastic component with a non-slip pad or grip attached, such that the label is configured to grip to a user's head or hair to improve stability of the headgear.

In accordance with certain embodiments disclosed herein, a headgear can comprise a single tubular strap comprising a first end, a second end, and a length therebetween. The headgear can also include a first and second substrate extending respectively in the first and second ends of the strap. Each of the first and second substrates can comprise a corresponding locking geometry configured to secure the strap on the first or second substrate.

In various embodiments, the strap can comprise elastic, knitted fabric. The first and second substrates can comprise moulded plastic. The first and second substrates can be semi-rigid. For each of the first and second substrates, the locking geometry can comprise an enlarged geometry on the substrate. For example, for each of the first and second substrates, the locking geometry can comprise tabs or arms configured to catch on an inner portion of the strap.

The headgear can further comprise a corresponding hook at the first and second ends of the strap. Each corresponding hook can be configured to attach the headgear to a mask. For each strap, the length of the strap can be configured to be adjusted by moving the strap over the locking geometry. In various embodiments, for each strap, the strap can bunch between the hook and the locking geometry.

For example, an embodiment of the headgear disclosed herein comprises a circular knitted strap that is configured to encase a substrate, wherein the substrate comprises a lock that induces increased friction between the substrate and the strap. The increased friction provided by the lock reduces the ease with which the strap can slide over the substrate and, thus, provides an adjustment mechanism for the length of the strap and the size of the headgear.

In accordance with certain embodiments disclosed herein, a headgear can comprise a pair of straps adjustably coupled to each other. The headgear can also include a buckle comprising a first end and a second end. The buckle can comprise an adjustment mechanism at each of the first and second ends to adjustably couple to a corresponding one of the pair of straps such that the pair of straps are adjustably coupled to each other. Each adjustment mechanism can comprise a pair of rotatable posts. In various embodiments, at least one of the pair of straps can comprise fabric. At least one of the pair of straps can comprise elastic material or inelastic material.

For example, an embodiment of the headgear disclosed herein comprises a buckle having two adjustment mechanisms configured to provide a way to adjustably connecting two elastic straps. The adjustment mechanisms comprise one or more rotating posts configured to reduce friction such that the straps slide through the buckle before they stretch.

In accordance with certain embodiments disclosed herein, a headgear can comprise at least one side strap. The side strap can comprise a plurality of regions, each region differing from the other regions in at least one property. The property can include elasticity, flexibility, density, or geometry. In some embodiments, the side strap has four regions. At least one region can be substantially elastic. At least one region can comprise laminated material. The laminated material can comprise neoprene. At least one region can comprise a curve above and forward of a user's ear. In one example, a first region can be a substantially straight region comprising laminated foam and fabric (e.g., Breath-O-Prene™), a second region can be a region comprising laminated foam and fabric (e.g., Breath-O-Prene™) with a dog-leg, a third region can be a region comprising an elastic strap, and a fourth region can be a region comprising laminated foam and fabric (e.g., Breath-O-Prene™). Compared to the laminated foam and fabric (e.g., Breath-O-Prene™) of the first and second regions, the laminated foam and fabric (e.g., Breath-O-Prene™) of the fourth region can have a lower density.

In some embodiments, the side strap can comprise two side straps. The two side straps can be adjustably connected at the rear of a user's head via a connector. For example, the connector can be a buckle. The headgear can comprise a length securement component that comprises a hook and loop type fastener.

As another example, a further embodiment of the headgear disclosed herein comprises single strap configuration, wherein two straps that comprise a plurality of regions with differing physical attributes are adjustably connected at the rear of a user's head.

In accordance with certain embodiments disclosed herein, a headgear can comprise a single tubular strap comprising a first strap end, a second strap end, and a length therebetween. The headgear can also comprise a resilient core housed within the strap. The resilient core can comprise a first core end and a second core end. In some embodiments, the strap can comprise a fabric. The strap can comprise elastic or inelastic material.

In some embodiments, each of the first strap end and the second strap end extends respectively beyond the first core end and the second core end of the resilient core. Each of the first strap end and the second strap end can pass through a corresponding connector configured to couple the headgear to a mask. The length of the strap can be configured to be adjusted by moving each of the first and second strap ends through a corresponding loop of the corresponding connector.

In some embodiments, the resilient core can be configured to extend around a back of a user's head. The resilient core can be configured to extend forward of a user's ears and rearward of the mask. The resilient core can comprise moulded plastic. Furthermore, the resilient core can comprise a three-dimensional structure that passes below a user's eyes and above a user's ears.

As yet another example, an embodiment of the headgear disclosed herein comprises a knitted elastic strap that is tubular and that is configured to encase a resilient core. The resilient core can be configured to extend around a rear of a user's head, between their cheeks, and can comprise a 'dog leg' or 's' shaped geometry to direct the strap away from the user's eyes and ears.

BRIEF DESCRIPTION OF THE DRAWINGS

FIG. 2a is a perspective view of a first embodiment of a headgear of the present disclosure.

FIG. 2b is a diagrammatic view of the adjustment of the headgear of FIG. 2a.

FIG. 3 is a perspective view of a first embodiment of the buckle of the headgear of FIGS. 2a and 2b.

FIG. 4 is a perspective view of the headgear of FIGS. 2a and 2b in a bifurcated arrangement.

FIG. 9a is a perspective view of a sixth embodiment of the buckle of e headgear of FIGS. 2a, 2b and 4.

FIG. 12a is a perspective view of a third embodiment of the label with integrated buckles of the headgear of FIG. 10.

FIG. 12b is a cross-sectional plan view of the third embodiment of the label with integrated buckles of the headgear of FIG. 10.

FIG. 15a is a perspective e of a fourth embodiment of the headgear of the present disclosure, worn by a user.

FIG. 15b is a cross-sectional diagrammatic view of the adjustment mechanism of the headgear of FIG. 15a.

FIG. 17 is a side view of a sixth embodiment of the headgear of the present disclosure, worn by a user.

DETAILED DESCRIPTION

Figure 1:
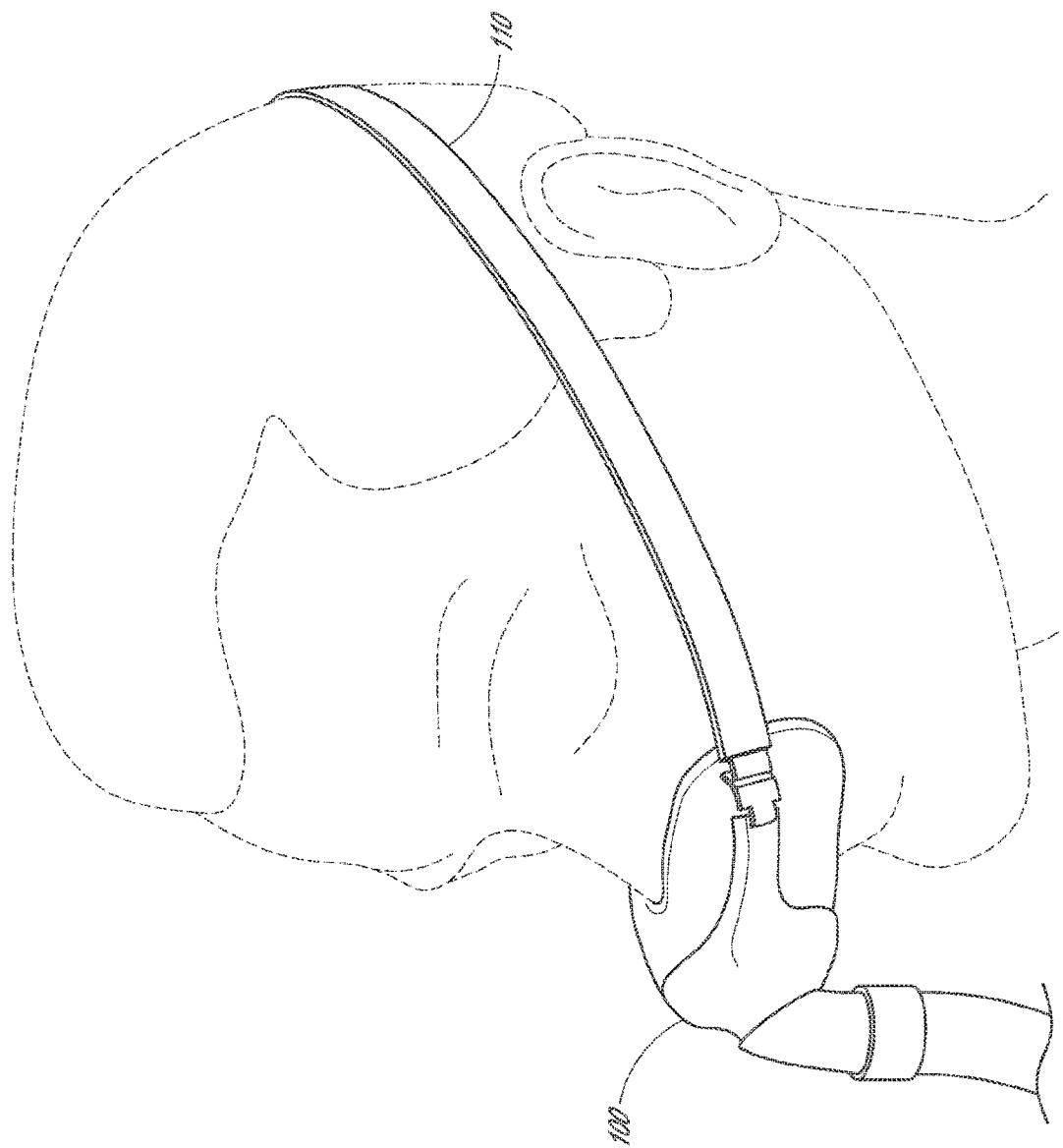
FIG. 1 is a perspective view of a nasal respiratory mask in use with a single strap elastic headgear.

Various embodiments of a headgear, e.g., for a respiratory mask, are configuration providing the benefits of a single strap configuration (e.g., low profile, unobtrusive, ease of use, etc.), yet are also configured to be stable on a user's head to reduce the risk of displacing the mask. Various embodiments described herein are also designed to conform to a user's face and/or head, to avoid discomfort from being too close to the user's eyes and ears, and to be adjustable. It is understood that one or more features described herein for one embodiment can be used with one or more features described herein for another embodiment.

Overlapping Straps Headgear:

FIGS. 2a and 2b show an example headgear 200 in accordance with certain embodiments described herein that is configured to provide improved adjustability and stability. In certain embodiments, the headgear 200, e.g., for a respiratory mask, can comprise a first strap 210, a second strap 220, and a pair of buckles 230, 240. The pair of buckles 230, 240 can include a corresponding buckle 230, 240 for the first and second straps 210, 220. In various embodiments, each of the first and second straps 210, 220 can comprise a first end, a second end, and a length therebetween. Each buckle 230, 240 can be configured to move along the length of the first or second strap 210, 220 to adjust the size of the headgear 200. In some embodiments, each of the first and second straps 210, 220 can be configured to connect to a respiratory mask 100 at the first end. Each of the first and second straps 210, 220 can also be configured to adjustably couple to the corresponding buckle 230 or 240. Furthermore, each of the first and second straps 210, 220 can be configured to be fixedly coupled to the other buckle 230 or 240 at the second end.

For example, as shown in FIGS. 2a and 2b, the headgear 200 comprises first and second straps 210, 220 and first and second buckles 230, first and second straps 210, 220 are configured to have two ends, wherein one end is provided with a connector, such as a hook or clip feature (not shown), that connects to a respiratory mask and the other end connects to one of the first or second buckles 230, 240. The first strap 210 is configured to connect to a respiratory mask at one end, pass through the first buckle 230, and permanently connect to the second buckle 240 at the other end. The second strap 220 is configured to connect to a respiratory mask at one end, pass through the second buckle 240, and permanently connect to the first buckle 230. The first and second straps 210, 220 are configured to overlap each other in a region between the first and second buckles 230, 240. The overlapping region is positioned at the rear of a user's head, in use. As shown in FIGS. 2a and 2b, the overlapping portions of the first and second straps 210, 220 in the region between the first and second buckles 230, 240 can allow the headgear 200 to have a configuration similar to a single strap configuration even though the headgear 200 comprises multiple straps 210, 220.

Further, although the headgear 200 has multiple straps 210, 220, the headgear 200 can be configured to be adjustable in length. For example, as shown in FIG. 2b, by moving the first and second buckles 230, 240 closer together, the amount of overlap between the first and second straps 210, 220 is reduced and the overall length of the headgear is increased. Moving the first and second buckles further apart has the reverse effect of increasing the overall length of the headgear 200. For example, by moving the first and second buckles 230, 240 further apart, the amount of overlap between the first and second straps 210, 220 is increased and the overall length of the headgear 200 is reduced. In other embodiments, by moving the buckles 230, 240 closer together, the overall length of the headgear is reduced, and by moving the buckles 230, 240 further apart, the overall length of the headgear is increased. In various embodiments, the length of the headgear 200 can be adjusted most easily when it is under tension, such as when it is being worn by a user.

The material, shape, size (e.g., length, width, thickness), color, and/or other physical properties of the first and second straps 210, 220 are not particularly limited, but can be based on the intended mask (e.g., relatively large, medium, or small in size), the intended user (e.g., adult, child, or infant) and/or expected force to counteract (e.g., relatively large, medium, or small in amount). The material, shape, size, color, and/or other physical properties of the first strap 210 can be the same as or different from those of the second strap 220. In certain embodiments, the first and/or second straps 210, 220 can comprise fabric, in some embodiments, the first and/or second straps 210, 220 can comprise a tubular shape. For example, in one embodiment, the first and/or second straps 210, 220 can be made from a length of knitted tubular elastic. In some embodiments, the straps 210, 220 may be made from any elastic or inelastic material, including, but not limited to, textiles, extruded or moulded plastics or laminated materials (e.g., a material comprising neoprene or Breath-o-Prene™).

FIG. 3 shows a non-limiting exemplary embodiment of the first and second buckles 230, 240. The first and second buckles 230, 240 comprise a glider portion (e.g., a glider end 300) and a strap attachment portion (e.g., a strap attachment end 310). The glider end 300 can be an end through which the first or second straps 210 or 220 can slide, e.g., allowing the size of the headgear to be adjusted. For example, in FIG. 3, the glider end 300 comprises a pair of substantially rectangular apertures 302 that are positioned adjacent to each other proximal to one end of the buckle 230, 240. The apertures 302 are offset from each other such that a post 304 is formed between them. The apertures 302 and the post 304 are configured to provide a torturous path through which one of the first or second straps 210, 220 may be threaded. The first or second strap 210, 220 is threaded through one aperture 302, over the post 304, and hack through the second aperture 302. Alternatively, the first or second strap 210, 220 is threaded through one aperture 302, under the post 304, and back through the second aperture 302 The dimensions of the apertures 302 and first and/or second strap, 210, 230 can be defined such that the friction forces induced between them restrict free movement of the strap through the glider end 300. The first or second buckle 230, 240 slides along the first or second strap 210, 220 via the glider end 300 when the user applies an intentional force to it but remains in a semi-fixed position under forces that are applied to the headgear 200 when it is being worn by a user. Accordingly, each buckle 230, 240 can be configured to move along the length of the first or second strap 210, 220 to adjust the size of the headgear 200.

The strap attachment end 310 is configured to be fixedly coupled, e.g., permanently attached in some instances, to one end of the first or second strap 210, 220. It is attached to which ever strap 210, 220 does not pass through the glider end 300. The attachment can be formed by over-moulding the buckle 300 to one end of the first or second strap 210, 220. In alternative embodiments, the attachment may be provided by other appropriate means, such as, hut not limited to welding, gluing, or a mechanical clip. The term 'welding,' as used herein, can refer to any type of welding commonly used to connect plastic components. In some embodiments, the attachment end 310 may include a further aperture through which the strap 210, 220 is threaded; the strap is theft secured to itself by sewing or any other appropriate technique.

The example buckle for the first and second buckles 230, 240 is shown in FIG. 3 as rectangular in shape with curved corners. However, the shape is not particularly limited. For example, the shape of the first and/or second buckle 230, 240 can be circular, ovular, regular or irregular polygonal, etc. Further, the material, size, color, and/or other physical properties of the buckles 230, 240 are not particularly limited. The material, shape, size, color, and/or other physical properties of the first buckle 230 can be the same as or different from those of the second buckle 240.

In addition, the apertures 302 and post 304 of the buckles 230, 240 are shown in FIG. 3 as rectangular. However, the shapes of the apertures 302 and post 304 are not particularly limited. For example, the shapes of the apertures 302 and/or post 304 can be circular, ovular, regular or irregular polygonal, etc. Further, the size of the apertures 302 and post 304 are not particularly limited. The shape and size of the apertures 302 and/or post 304 of the first buckle 230 can be the same as or different front those of the second buckle 240. Additionally, the example buckle for the first and second buckles 230, 240 is shown in FIG. 3 as having two apertures 302 and one post 304. However, in some embodiments, the first and/or second buckle 230, 240 can have more than two apertures 302 and/or more than one post 304, e.g., to provide a more torturous path through which the first and/or second straps 210, 220 may be threaded. Further, the shape and size of the apertures 302 and/or posts 304 within a buckle 230 or 240 can be the same as or different from each other.

Some embodiments of the buckles 230, 240 may have a plurality of apertures 302 but can be used with the first or second strap 210, 220 only going through one of the apertures 302. In some embodiments, the first and/or second buckle 230, 240 have only one aperture 302.

FIG. 4 shows how the headgear 200 can provide improved stability on the user's head. For example, the headgear 200 can be configured to be adapted between a first and a second configuration. The first configuration can comprise portions of the first and second straps 210, 220 overlapping in a region between the first and second buckles 230, 240 (see, e.g., FIG. 3). The second configuration, as shown in FIG. 4, can comprise the portions of the first and second straps 210, 220 bifurcating in the region between the first and second buckles 230, 240. The overlapping first and second straps 210, 220 are moved apart from each other on the user's head, such that a bifurcated headgear configuration is provided. The bifurcated configuration provides additional contact points on the user's head, which may counteract additional force vectors and thus minimize the likelihood of the headgear 200 moving up and/or down and displacing the respiratory mask on the user's face. The first and second buckles 230, 240 provide pivot points at which the first and/or second straps 210, 220 bend at an angle to sit lower or higher on the hack of the user's head. As seen in FIG. 4, the bifurcation of the first and second straps 210, 220 results in misalignment of the straps within the buckles 230, 240. This misalignment may, in some cases, cause bunching in the strap, which may restrict adjustments to the length of the headgear whilst it is in the bifurcated configuration. Advantageously, in various embodiments, the headgear 200 can include multiple straps to provide a stable headgear, yet can be configured to adjust the size of the headgear 200. Further, in some embodiments, the headgear 200 can be adjusted while in the bifurcated configuration.

FIGS. 5 to 9 show a variety of ion-limiting exemplary embodiments of buckles that may be used in a headgear configuration such as that described in relation to FIGS. 2 and 4. In such embodiments, the first and/or second buckles 230, 240 can include a pivot connection between the glider portion and the strap attachment portion. For example, each of these buckles comprises two components that are pivotally connected. The pivotal connection allows the headgear to be used in a bifurcated arrangement with reduced bending of the straps and also isolates the glider function of the glider portion of the buckle from the fixed strap connection of the strap attachment portion. This consequently allows the length of the headgear to be adjusted whilst in bifurcated arrangement.

Figure 5:
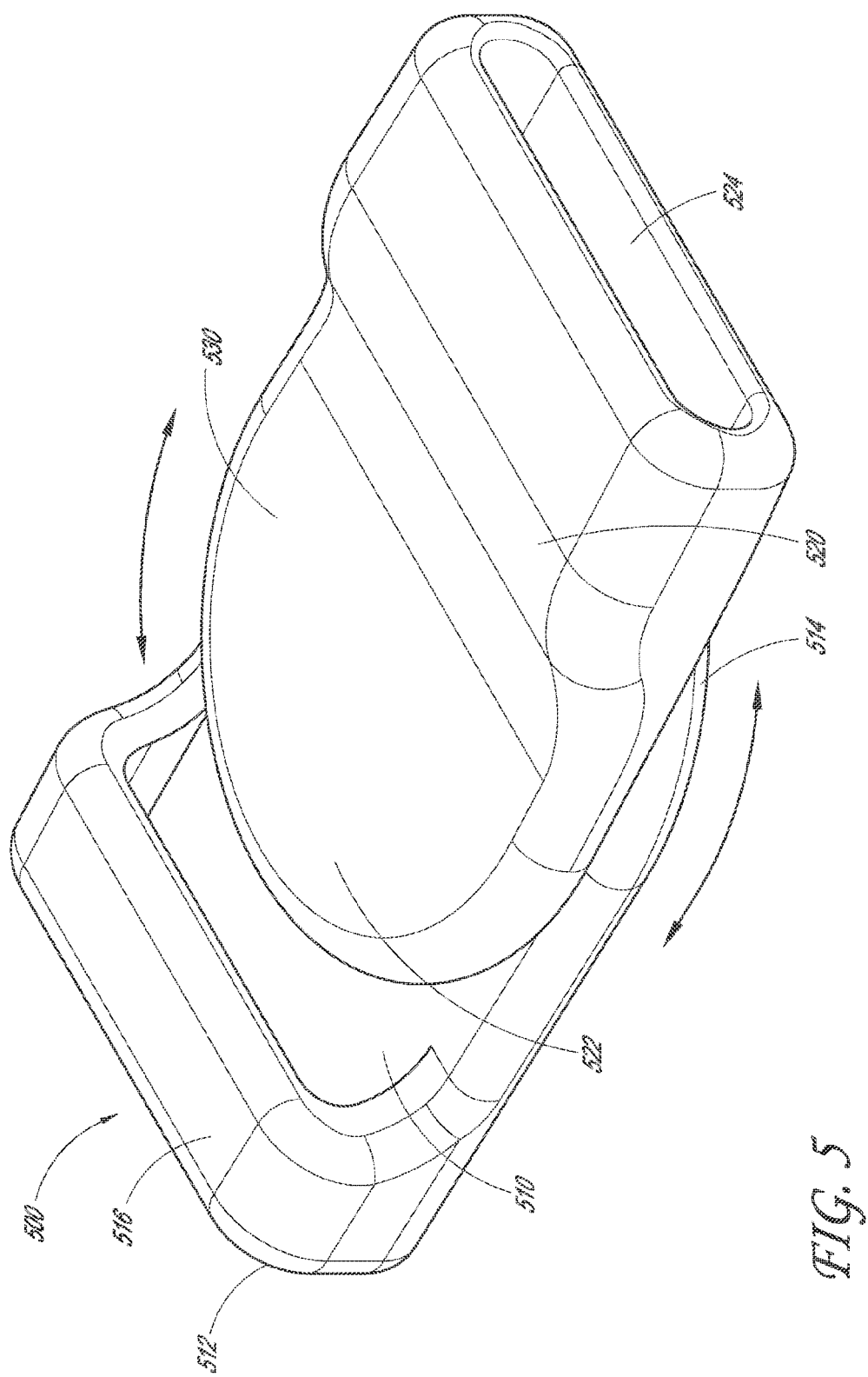
FIG. 5 is a perspective view of a second embodiment of the buckle of the headgear of FIGS. 2a, 2b and 4.

The buckle 500 of FIG. 5 comprises a glider portion (e.g., a glider half 510), a strap attachment portion (e.g., a fixed strap half 520), and a pivot connection 530. The glider half 510 comprises a strap end 512, which has a substantially rectangular profile, and a glider pivot end 514, which has a semi-circular profile, at the opposing end. The strap end 512 comprises a loop 516 through which the first or second strap 210, 220 is configured to pass. The loop 516 may apply a friction force to the first or second strap 210, 220 such that the buckle 500 only slides along the strap when an intentional force is applied. The glider pivot end 514 can be configured to connect with a corresponding fixed pivot end 522 of the fixed strap half 520.

The fixed strap half 520 comprises the fixed pivot end 522 at one end and a strap connection 524 at the opposing end, wherein the fixed pivot end 522 has a semi-circular profile and the strap connection has a substantially rectangular profile. The pivot connection 530 can be located at the semi-circular profile ends of the glider half and fixed strap half (e.g., at the glider pivot end 514 and the fixed pivot end 522). In this example, the semi-circular profile ends 514, 522 overlap such that the overall profile of the buckle 500 has a rectangular profile. The strap connection 524 comprises an opening that is configured to receive an end of the first or second strap 210, 220. The end of the first or second strap 210, 220 is fixedly coupled, e.g., permanently fixed in some instances, within the strap connection 524 in any suitable way, such as, but not limited to, over-moulding or welding. The pivot connection 530 comprises geometry on both the glider half 510 and the fixed strap half 520 (not shown) that allows the glider half and the fixed strap half to rotate relative to each other, as shown by the arrows. In some embodiments, the geometry of the pivot connection 530 may include a snap-fit dome and ring configuration (not shown). When assembled within the headgear 200, the first or second strap 210, 220 passes through the loop 516 and over the fixed pivot end 522 of the fixed strap half 520.

Figure 6:
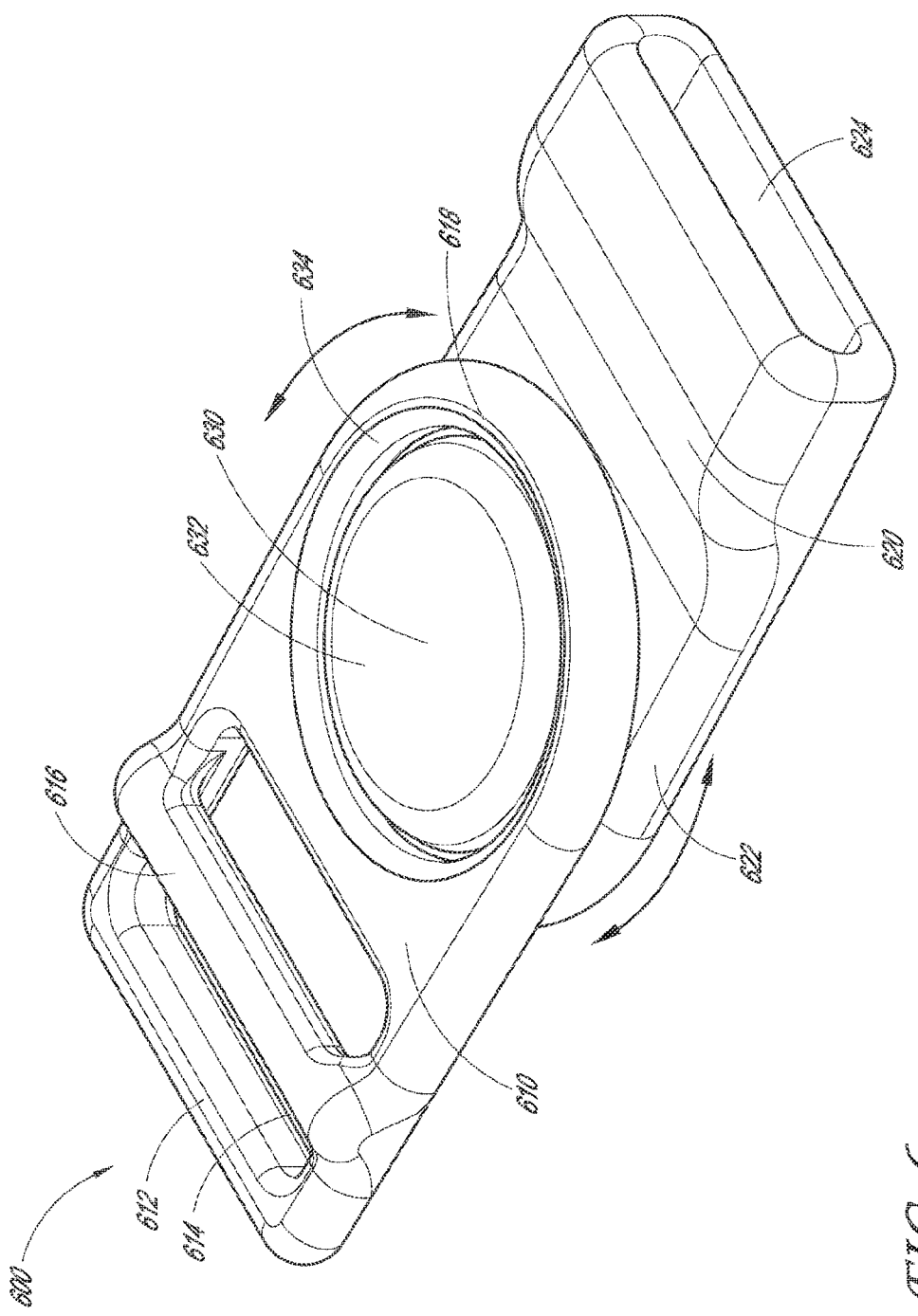
FIG. 6 is a perspective view of a third embodiment of the buckle of the headgear of FIGS. 2a, 2b and 4.

FIG. 6 provides another embodiment of a buckle 600. The illustrated embodiment comprises a glider portion (e.g., a glider half 610), a strap attachment portion (e.g., a fixed strap half 620), and a pivot connection 630. The glider half 610 has a strap end 612, which has a rectangular profile and comprises a rectangular aperture 614 with a raised cross-bar 616. The strap end 612 is configured to provide a torturous path through which the first or second strap 210, 220 passes. The first or second strap 210, 220 passes through the aperture 614, and beneath (or above) the raised cross-bar 616, thereby allowing for adjustment of the buckle 600 position along the length of the strap 210 or 220. The raised cross-bar 616 is configured to apply a friction force to the first or second strap 210, 220 that passes beneath it. The raised cross-bar 616 may provide for a lower profile headgear compared to that discussed above. The glider half 610 also comprises a glider pivot end 618 that has a semi-circular profile and is configured to connect with a corresponding fixed pivot end 622 of the fixed strap half 620.

The fixed strap half 620 comprises the fixed pivot end 622 at one end and a strap connection 624 at the opposing end. The fixed pivot end 622 has a semi-circular profile and the strap connection 624 has a substantially rectangular profile. The pivot connection be located at the semi-circular profile ends of the glider half and fixed strap half (e.g., at the glider pivot end 618 and the fixed pivot end 622). In this example, the semi-circular profile ends 618, 622 overlap such that the overall profile of the buckle 600 has a rectangular profile. The pivot connection 630 comprises a snap-fit dome 632 and a snap-fit ring 634, wherein the snap-fit ring 634 is configured to receive and rotate about the snap-fit dome 632. The snap-fit dome 632 is configured to form part of the fixed strap half 620 and the snap-fit ring 634 forms part of the glider half 610. The illustrated snap-fit dome 632 is substantially mushroom shaped.

Figure 7:
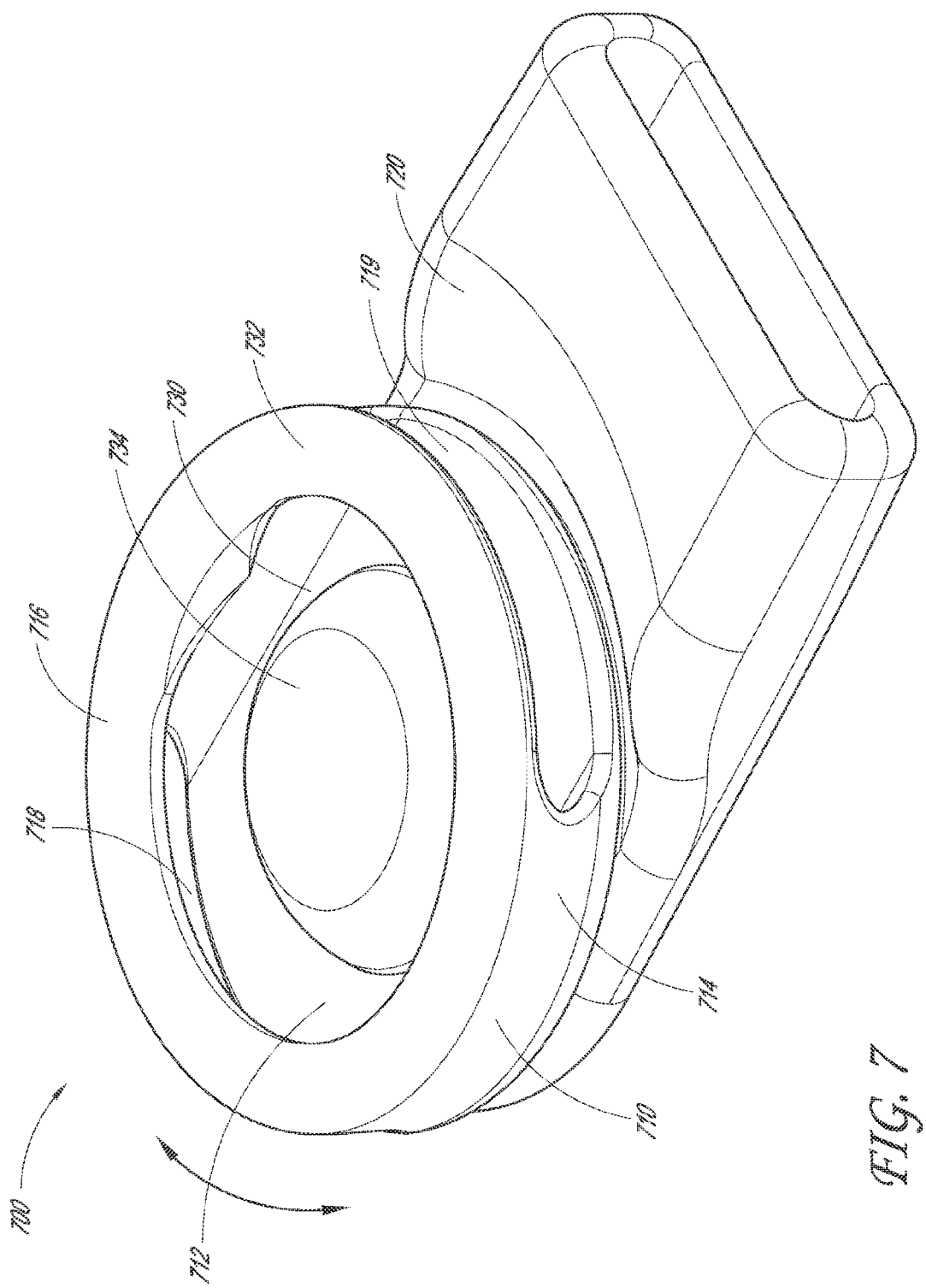
FIG. 7 is a perspective view of a fourth embodiment of the buckle of the headgear of FIGS. 2a, 2b and 4.

FIG. 7 shows an embodiment of a buckle 700 comprising a glider half 710 a fixed strap half 720 and a pivot connection 730. The glider half 710 has a circular profile. The glider half 710 comprises an inner surface 712, a substantially cylindrical side wall 714 and a ring shaped outer surface 716. The inner surface 712 comprises a substantially planar bearing surface that contacts a corresponding bearing surface on the fixed strap half 720 and forms the snap-fit ring 732 of the pivot connection 730. The cylindrical side wall 714 comprises an entry slot 718 and an exit slot 719 through which the first or second strap 210, 220 extends radially across the diameter of the glider half 710. The outer surface 716 is configured to retain the first or second strap 210, 220 within the glider half 710.

The pivot connection 730 comprises the snap-fit ring 732 and a snap-fit dome 734. The snap-fit ring is 732 configured to receive and rotate about the snap-fit dome 734, which has a substantially mushroom shaped geometry in the illustrated configuration. The snap-fit dome can be configured to extend into the centre of the glider half 710 such that it impinges upon, and applies a friction force to, the first or second strap 210, 220 as the strap passes through the slots 718 of the glider half 710.

Figure 8:
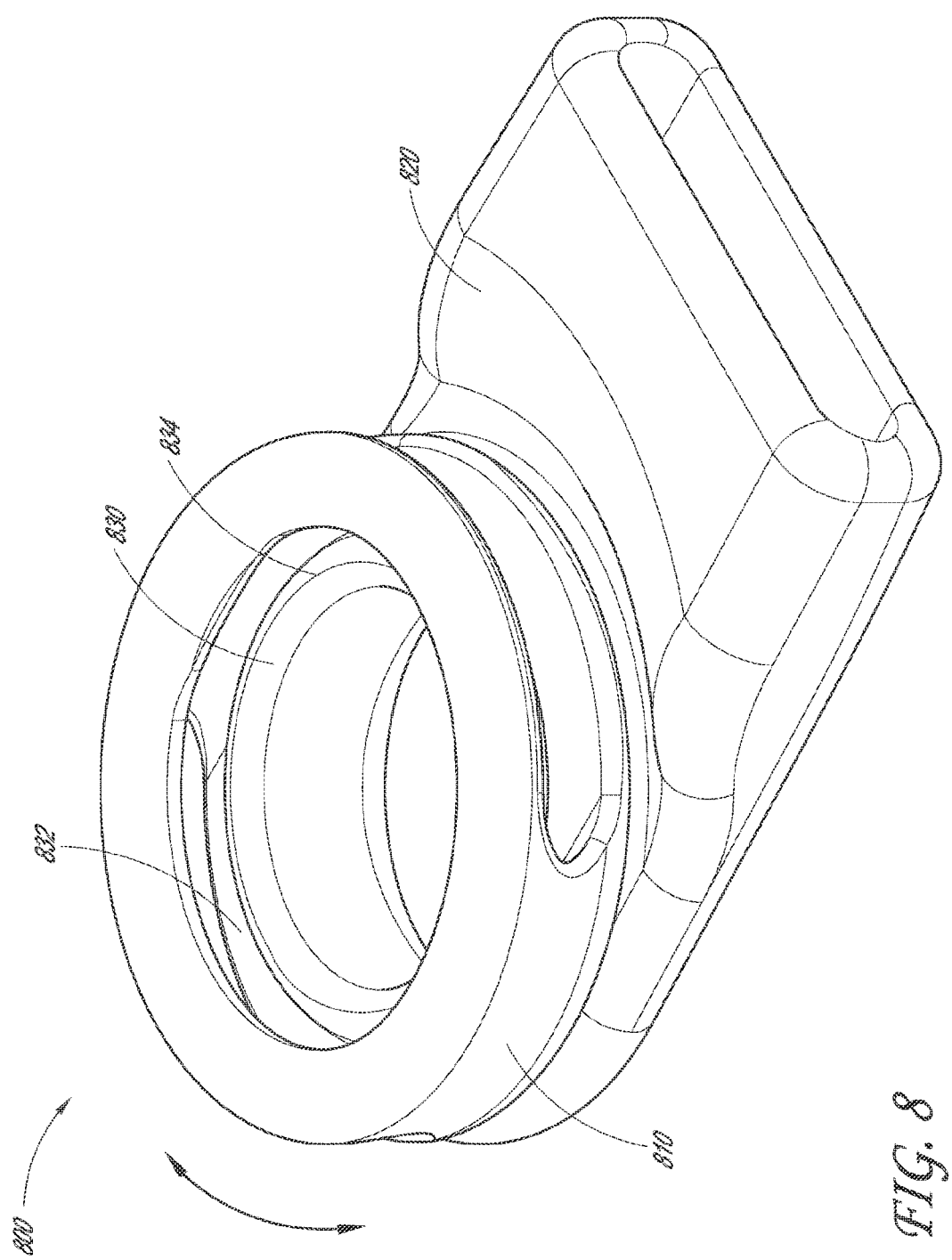
FIG. 8 is a perspective view of a fifth embodiment of the buckle of the headgear of FIGS. 2a, 2b and 4.

The buckle 800 shown in FIG. 8 has a pivot connection 830 that comprises a snap-fit female ring 832 and a snap-fit male ring 834. The snap-fit female ring 832 can be configured in any suitable manner, including the same as the snap-fit ring 732 of the previous embodiment. The snap-fit male ring 834 differs from snap-fit dome 734 in that a circular hole extends through the centre. The circular hole results in the snap-fit male ring having a cylindrical wall that is pivotally received by the snap-fit female ring 832. This configuration may make it easier in some embodiments to connect the glider half 810 to the fixed strap half 820 as a result of the cylindrical wall of the snap-fit male ring 834 flexing during insertion into the snap-fit female ring 832. The snap-fit dome 734 of the previous embodiment can be a solid component that cannot flex in some embodiments. This configuration also provides an appearance that is similar on both sides of the buckle, which may reduce or eliminate the likelihood of user confusion.

Figure 9B:
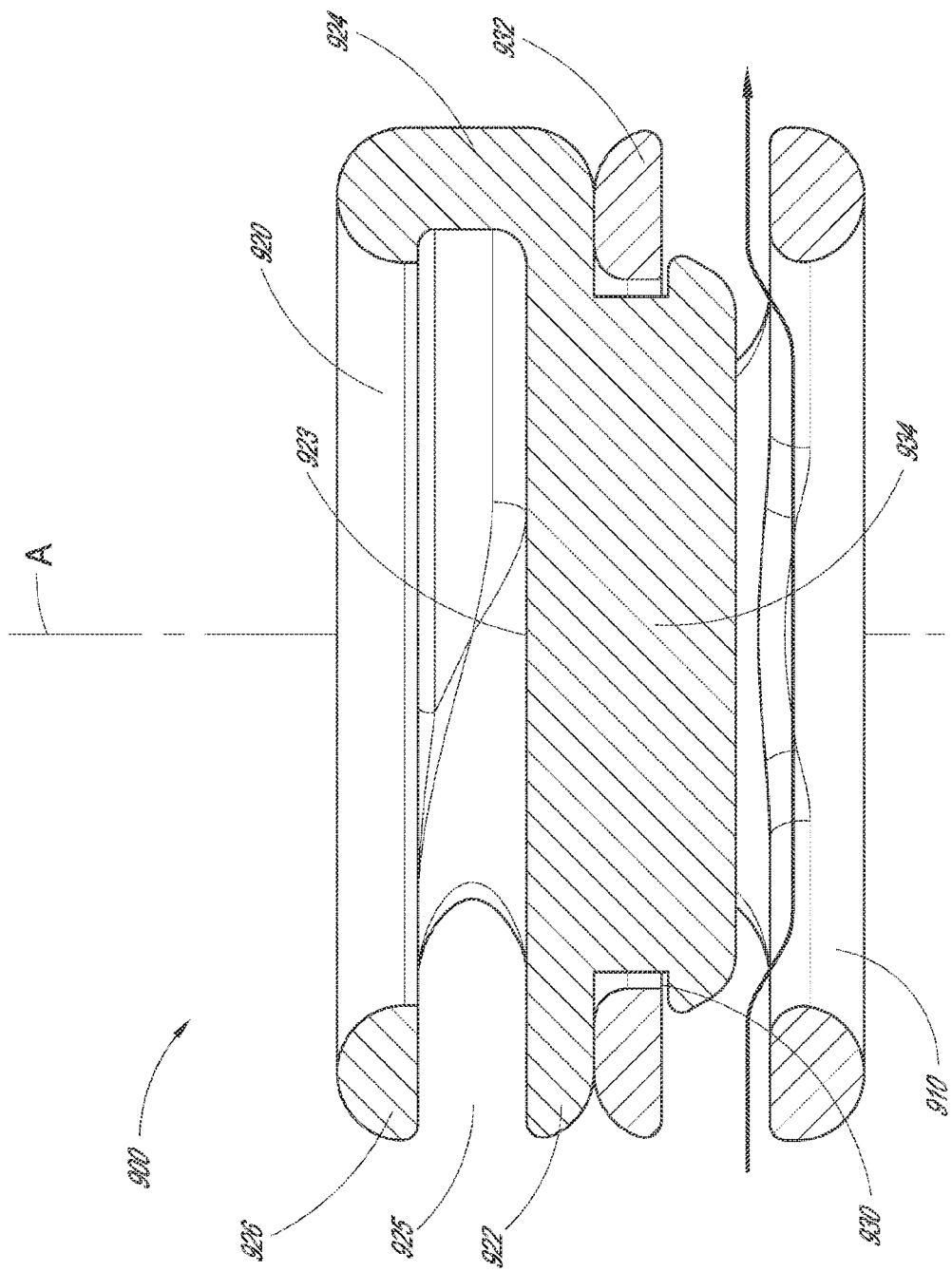
FIG. 9b is a cross-sectional view of the sixth embodiment of the buckle of the headgear of FIGS. 2a, 2b and 4.

FIGS. 9a and 9b show an embodiment of a buckle 900 wherein both glider and fixed strap halves 910, 920 are substantially (e.g., completely) circular in profile. The circular profiles can overlap such that the buckle 900 can form a single circular profile. The buckle comprises a glider half 910 and a fixed strap half 920 that are pivotally connected through a central axis A. The glider half 910 can be similar to the glider halves 710 and 810 of the previous embodiments. The fixed strap half 920 can be similar in geometry to the glider half 910. The fixed strap half 920 can be substantially cylindrical and comprises an internal wall 922, a side wall 924 and an outer ring 926. The internal wall comprises a snap-fit dome 934 and a strap connection surface 923. The snap-fit dome 934 forms part of the pivot connection 930 and is configured to be received by the snap-fit ring 932 of the glider half 910. It can be seen in FIG. 9b that the snap-fit dome 934 has a substantially mushroom shaped cross-section, which extends into the glider half 910 such that it interferes with the strap path (indicated by the arrow). The snap-fit dome 934 causes the first or second strap 210, 220 to follow a torturous path, which causes friction forces between the strap and the buckle 900, thus providing controlled movement of the buckle 900.

The strap connection surface 923 is configured to provide a substantially flat surface to which the end of the first or second strap 210, 220 is fixedly coupled, e.g., permanently secured via welding. In some embodiments, the end of the first or second strap 210, 220 may be connected to the fixed strap half 920 by other methods, such as, but not limited to, adhesives or over-moulding.

The side wall 924 comprises a cylindrical wall extends between the perimeter of the internal wall 922 and the perimeter of the outer ring 926. The side wall 924 also comprises an entry slot 925 through which the first or second strap 210, 220 passes before being secured to the strap connection surface 923.

The outer ring 926 is configured to further secure the end of the first or second strap 210, 220 within the fixed strap half 920. The outer ring 926 comprises a central opening that is configured to expose a portion of the first or second straps 210, 220. The exposed strap portion may provide some cushioning against the users head, in use, and may provide an appearance that matches the glider half 910. It is beneficial for the appearance of the glider half 910 and the fixed strap half 920 to be generally the same because it means that the buckle 900 is reversible. The reversibility of the buckle 900 means that it can be used as both a first and second buckle without the need to produce separate 'left' and 'right' configurations. The buckles 900 can be alternated so that one has the glider half 910 proximal to the user's head and the other has the fixed strap half 920 proximal to the user's head.

Accordingly, certain embodiments of a headgear, e.g., for a respiratory mask, can include multiple straps 210, 220 and a pair of buckles that provide a stable headgear that can adjust the size of the headgear. As described herein, the material, shape, size, color, and/or other physical properties of the first or second straps 210, 220 are not particularly limited. The first and second straps 210, 220 can include a first end, a second end, and a length therebetween. The pair of buckles can include a corresponding buckle for the first and second straps 210, 220. The pair of buckles can include two buckles that are substantially similar to each other. However, it would be understood that the buckles can be different from each other.

In various embodiments, the headgear can be configured to be adapted between a first and second configuration. For example, the first configuration can be similar to a single strap configuration, e.g., portions of the first and second straps 210, 220 overlapping in a region between the pair of buckles. The second configuration can be a bifurcated configuration, portions of the first and second straps 210, 220 bifurcating in the region between the pair of buckles. In some such embodiments, the pair of buckles can be configured to adjust the size of the headgear while in the bifurcated configuration.

In some such embodiments, each of the buckles can include a glider portion, a strap attachment portion, and a pivot connection therebetween. Each of the first and second straps 210, 220 can be configured to connect to a respiratory mask at the first end, to adjustably couple to the corresponding buckle at the glider portion, and to be fixedly coupled to the strap attachment portion of the other buckle at the second end. Each buckle can be configured to move along the length of the first or second strap 210, 220 to adjust the size of the headgear 200.

The material, shape, size, color, and/or other physical properties of the glider and/or strap attachment portions are not particularly limited. The material, shape, size, color, and/or other physical properties of the glider portion can be the same as or different from those of the strap attachment portion. Various modifications to the straps 210, 220 and/or buckles can be made.

Figure 10:
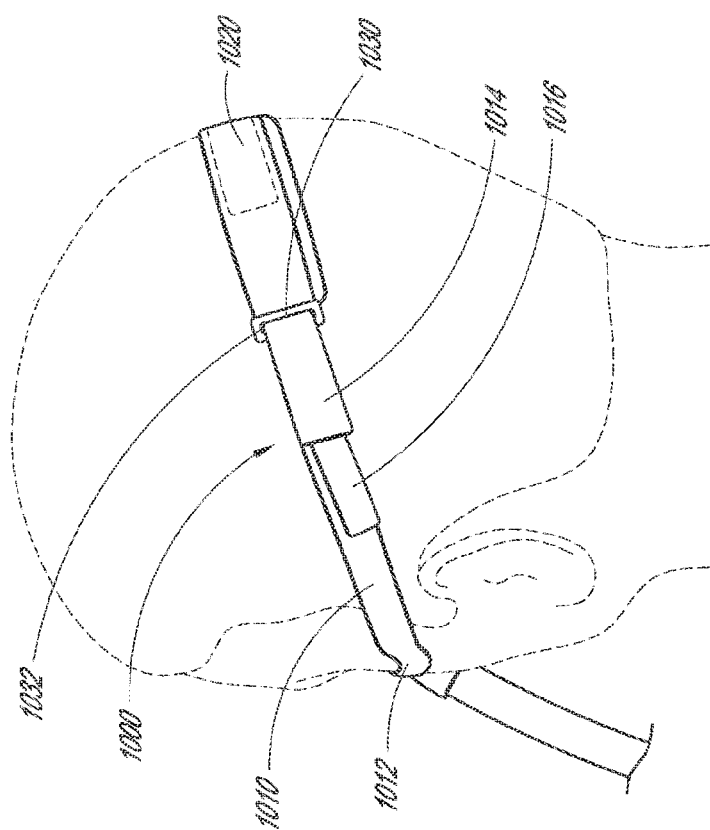
FIG. 10 is a perspective view of a second embodiment of a headgear of the present disclosure, worn by a user.

Combined Label Buckle:

In certain embodiments, a headgear, e.g., for a respiratory mask, can include a first strap and a second strap. Each of the first and second straps can comprise a mask connection portion, an adjustment portion, and a length therebetween. The headgear can also include a linking member between the first and second straps. The linking member can comprise a first end and a second end. The linking member can be coupled to the adjustment portion of the first strap via a first buckle at the first end and coupled to the adjustment portion of the second strap via a second buckle at the second end. For example, FIG. 10 shows a headgear 1000 comprising a pair of side straps 1010 (only one is visible, but another side strap 1010 is provided on the other side of the user's face), a linking member (e.g., a label 1020), and a pair of buckles 1030 (only one is visible). In some embodiments, one or more of the side straps 1010 are made of a tubular structure, such as a tubular knitted covered elastic, and comprise a mask connection portion (e.g., a mask end 1012), an adjustment portion (e.g., an adjustment end 1014), and a fastening tab 1016. The tubular structure can be knitted or formed into a tube by some other method (e.g., by sewing). At least one of the straps 1010 can comprise a semi-rigid substrate, and the tubular structure can be configured to move over the semi-rigid substrate at a corresponding mask end 1012. In various embodiments, the semi-rigid substrate can form a connection to the mask and provide a structure that helps keep the straps 1010 below the user's eyes. For example, in some embodiments, the mask end 1012 is configured to connect to a semi-rigid substrate, such as a connector or hook (not visible) or other feature that provides a connection to a respiratory mask. The mask end 1012 has an open end, such that the tubular side strap 1010 can be slid over an elongate hook structure (shown by the curve in the side strap 1010 proximal to the mask end 1012). The mask end 1012 is held in place by friction between the hook and the side strap 1010. In other embodiments, the mask end 1012 may be connected to a hook or connection feature by any other appropriate method, including, but not limited to, over moulding or a mechanical clip.

The adjustment end 1014 is configured to pass freely through the buckle 1030 and fold back on itself before being secured in place by the fastening tab 1016. The overall size of the headgear 1000 is determined by how much of the adjustment end 1014 is folded back on itself. For example, the straps 1010 can be adjusted by pulling the adjustment ends of the straps 1010. The fastening tab 1016 comprises the hook component of a 'hook and loop' fastening system, such as Velcro™. It is configured to attach to the side strap, which forms the loop component of the fastening system, thus setting and securing the length of the side strap 1010 and the size of the headgear 1000. In alternative embodiments, the adjustment end may be secured by other means, such as a mechanical clip or a buckle that provides a torturous path.

In various embodiments, the label 1020 comprises an elongate textile member that is substantially inelastic in comparison to the side straps 1010. For example, die label 1020 can include a fabric strap. In use, the label 1020 is configured to extend laterally across the rear of the user's heading some embodiments, the label 1020 has company branding applied to its outer surface. The label 1020 can include an overmoulded or printed grip, e.g., a grip to help maintain the position of the headgear on the user's head. In some embodiments, the label 1020 can include a plastic component, e.g., a moulded plastic component. The label 1020 can have a degree of flexibility configured to allow the label 1020 to conform to the user's head, e.g., for comfort. As examples, the label 1020 may comprise a non-slip pad (not shown) made from a material, such as, but not limited to, silicone, thermoplastic elastomer (TPE), or thermoplastic polyurethane (TPU), herein the pad is permanently attached to the label by means, such as, but not limited to, sewing or gluing. In alternative embodiments, the label 1020 can comprise an elastic textile, or other suitable material, such as a closed cell foam or plastic.

In certain embodiments, one or both of the pair of buckles 1030 can be separate components from the label 1020. For example, the buckles 1030 can be substantially rigid plastic components that comprise a loop 1032, through which the side straps 1010 are configured to pass, and an attachment tab (not visible). The loop 1032 has a substantially rectangular profile; however, in alternative embodiments, other geometries may be used. In some embodiments, the attachment tab (not visible) is configured to be fixedly 10) coupled, e.g., permanently connected, to the label 1020. For example, the buckles 1030 can be configured to be permanently attached to each of the lateral ends of the label 1020, such that the label and buckles 1030 form a single component. The connection may be formed by welding, sewing, gluing, over-moulding or any other appropriate method.

Figure 11:
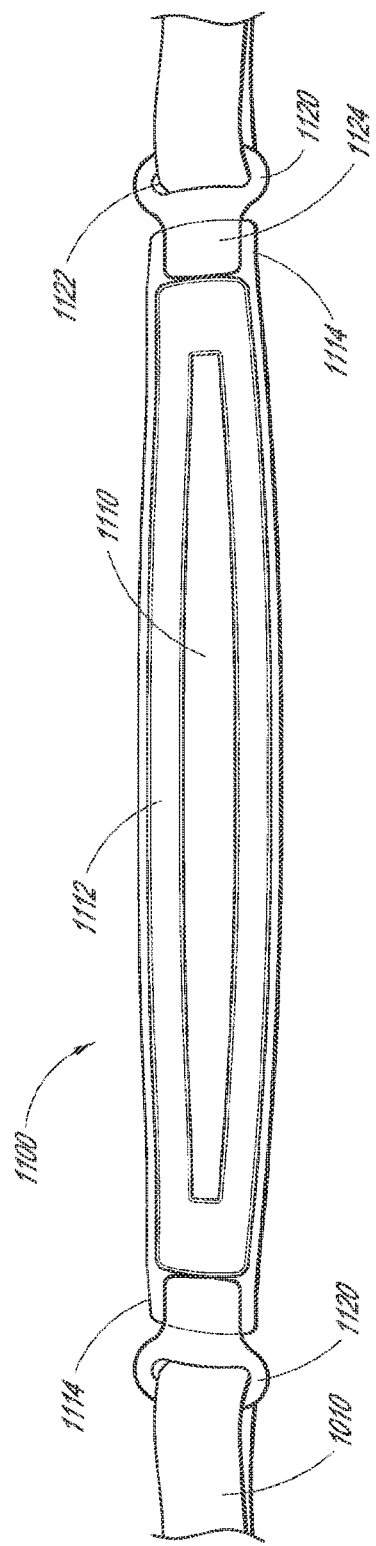
FIG. 11 is a front view of a second embodiment of label with integrated buckles of the headgear of FIG. 10.

FIG. 11 shows an alternative embodiment of a label 1100 with integrated buckles that may be used in combination with the headgear 1000 shown in FIG. 10. In some such embodiments, being integrally formed can reduce assembly and manufacturing costs. The label 1100 with integrated buckles comprises a label 1110 and a pair of buckles 1120. In some embodiments, the label 1110 comprises a symmetrical elongate textile component, wherein the long edges have a convex curve, such that the middle of the label is wider than the lateral ends 1114. The label 1110 also comprises a grip 1112 located on one side. The grip 1112 comprises a silicone. TPE, or TPU pad that substantially follows outline of the label 1110. The grip is configured to provide a non-slip surface that, in use, grips the user's head or hair, such that the headgear 1000 is stable and is less likely to slip down and displace the respiratory mask. The grip 1112 may be applied to the label 1110 using any suitable techniques, such as, but not limited to, screen printing, pad printing, and over-moulding.

The buckles 1120 comprise a loop 1122 at one end and an attachment tab 1124 at the opposing end. The loop 1122 comprises an elongate opening through which the side straps 1010 freely pass. The tab is configured to be fixedly coupled, e.g., permanently fixed, to the label 1110 via any suitable process, such as, but not limited to, welding.

FIGS. 12a and 12b show a third embodiment of a label 1200 with integrated buckles that can be used in combination with the headgear 1000 shown in FIG. 10. The label 1200 comprises integrated buckles 1220 and an elongate body 1210 configured to be moulded from a flexible and resilient material, such as silicone or a TPE, with a textured surface. The textured surface on such a material provides a relatively high level of friction with the user's head, which helps to maintain the placement of the headgear 1000. The elongate body 1210 has a three-dimensional structure that is curved along its length, such that it substantially matches the curvature of the rear of a user's head. The elongate body 1210 has a stepped geometry 1212 at each of the lateral ends 1214, wherein the cross-sectional wall thickness of the elongate body is reduced. This stepped geometry 1212 forms part of an integrally moulded buckle 1220 in combination with a crossbar 1222 that is offset from the stepped geometry 1212. The buckles 1220 are configured such that a side strap 1010 passes between the stepped geometry 1212 and the crossbar 1222 and then folds back on itself, thereby following a torturous path. The clearance between the stepped geometry 1212 and the crossbar 1222 is such that an intentional force has to be applied to the side strap 1010 in order to overcome the friction forces and pull the strap through the buckle 1220, thereby adjusting the size of the headgear 1000.

Figure 13B:
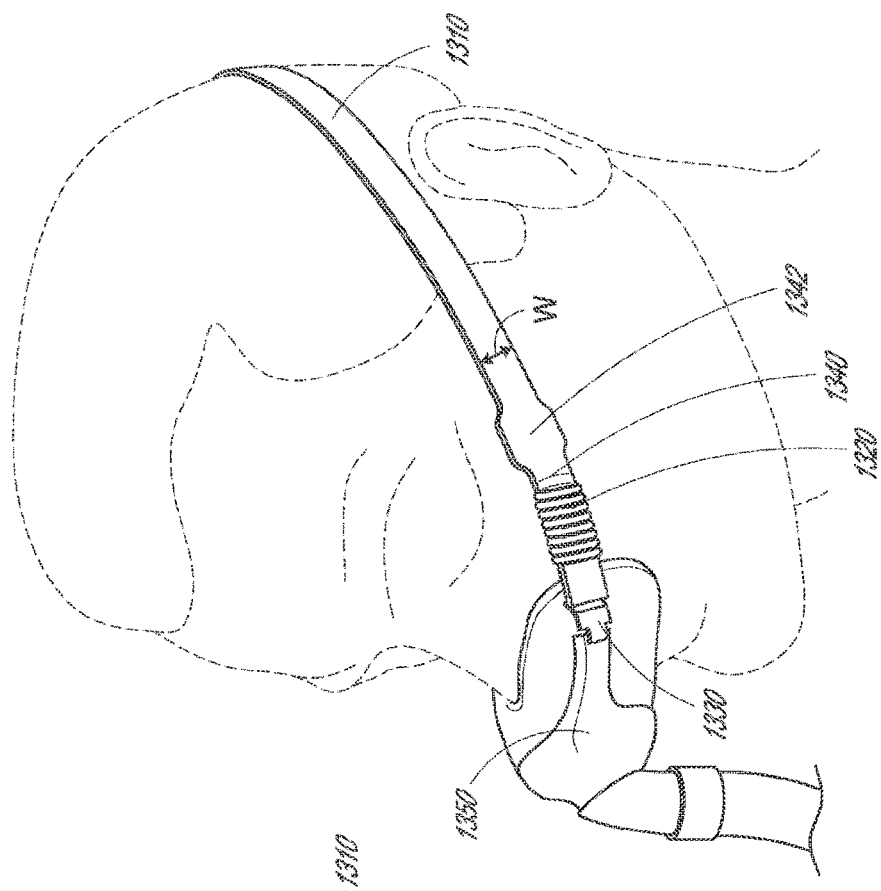
FIGS. 13a and 13b are perspective views of a thud embodiment of the headgear of the present disclosure, worn by a user.
Figure 13A:
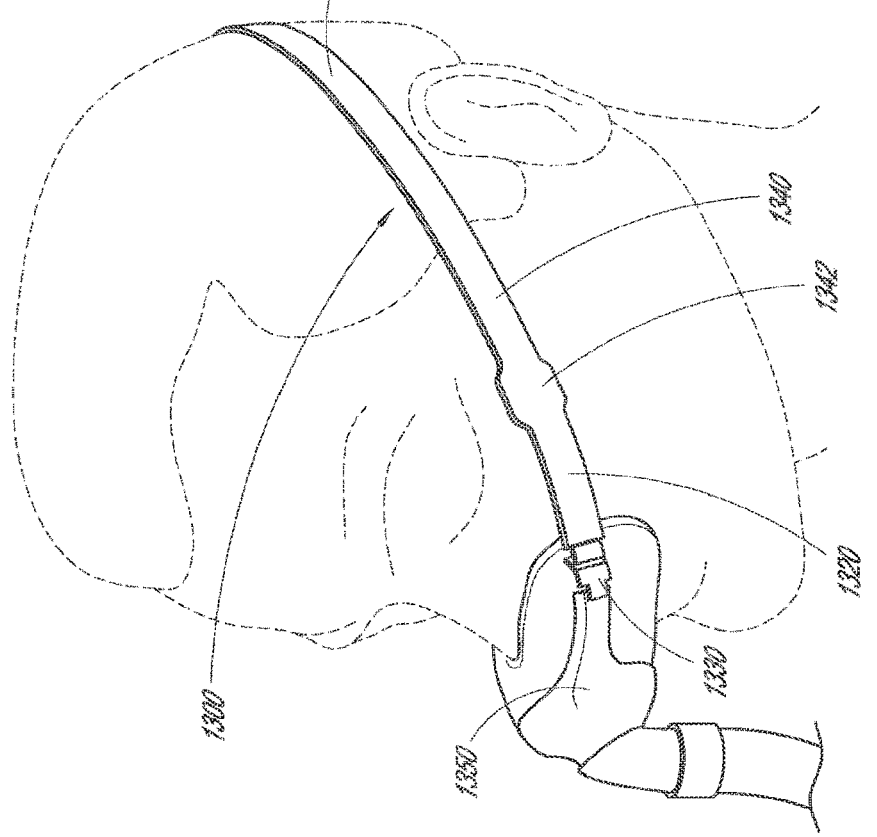

Bunched Adjustment:

In certain embodiments, a headgear, e.g., for a respiratory mask, includes a single tubular strap comprising a first end, a second end, and a length therebetween. A first and/or a second substrate can extend respectively in the first and second ends of the strap. The first and/or the second substrate can comprise a corresponding locking geometry configured to secure the strap on the first and/or second substrate. The length of the strap can be adjusted by moving the strap over the locking geometry. For example, FIGS. 13a and 13b show a headgear 1300 comprising a strap 1310 and a pair of mask connectors 1320 (only one is visible). Only one side of the strap 1310 is described herein, but it would be understood that the other side of the strap 1310 Call be similar or different. The strap 1310 can comprise elastic, knitted fabric. For example, in some embodiments, the strap 1310 comprises a circular knitted elastic sheath that is configured to have an opening at each end. The mask connectors 1320 comprise a hook 1330 at one end and an elongate substrate 1340 (inside strap 1310) at the other end, wherein the hook 1330 is configured to connect to a mask frame 1350 and the substrate 1340 is configured to be inserted into and retain the strap 1310.

In various embodiments, the substrate 1340 comprises an elongate member that is wider than it is thick. It may include a curved geometry that allows it to substantially match the curve of a user's cheek. The substrate 1340 can comprise a moulded plastic. In some embodiments, the substrate 1340 is made from a solid hut somewhat flexible material, such as nylon, polypropylene, or polycarbonate. Flexibility is desirable in a direction that is normal to the user's cheeks because it allows the substrate to better match the facial geometry of individual users. The flexibility of the substrate is relative to its thickness. The width W of the substrate 1340 can be such that flexibility in a vertical direction (when being worn by a user whilst sitting upright) is limited. Restricted vertical flexibility can improve the stability of the mask seal on the user's face. The substrate 1340 can rest against a user's cheek and can act as a brace that restricts twisting and bending of the strap 1310. Accordingly, in various embodiments, the substrate 1340 is semi-rigid to provide structure and conformance to the user's face and to help keep the strap 1310 away from the user's eyes and ears.

The substrate 1340 also comprises a locking geometry that comprises an enlarged geometry (e.g., a lock 1342 that is positioned approximately near a middle of the substrate length). The enlarged geometry can provide increased friction with the strap 1310. For example, in some embodiments, the lock 1342 comprises a section of the substrate 1340 that is wider than the strap 1310. The width of the lock 1342 is such that the strap 1310 has to stretch over the lock 1342, which causes the friction between the strap 1310 and the substrate 1342 to be greatly increased at this location. The friction is substantial enough to reduce or eliminate the likelihood of the strap 1310 being pulled over the lock 1342 when the headgear is being worn during normal use. As such, the lock 1342 is configured to provide a means of adjusting the length of the strap 1310 and, thus, the overall size of die headgear 1300. To reduce the size of the headgear 1300, the strap 1310 is pushed forward over the lock 1342, towards the hook 1330. Depending on the desired size, this can result in the strap bunching up between the hook 1330 and the lock 1342, as shown in FIG. 13b. To increase the size of the headgear 1300, the strap 1310 can be pulled over the lock 1342, away from the hook 1330.

Figure 14:
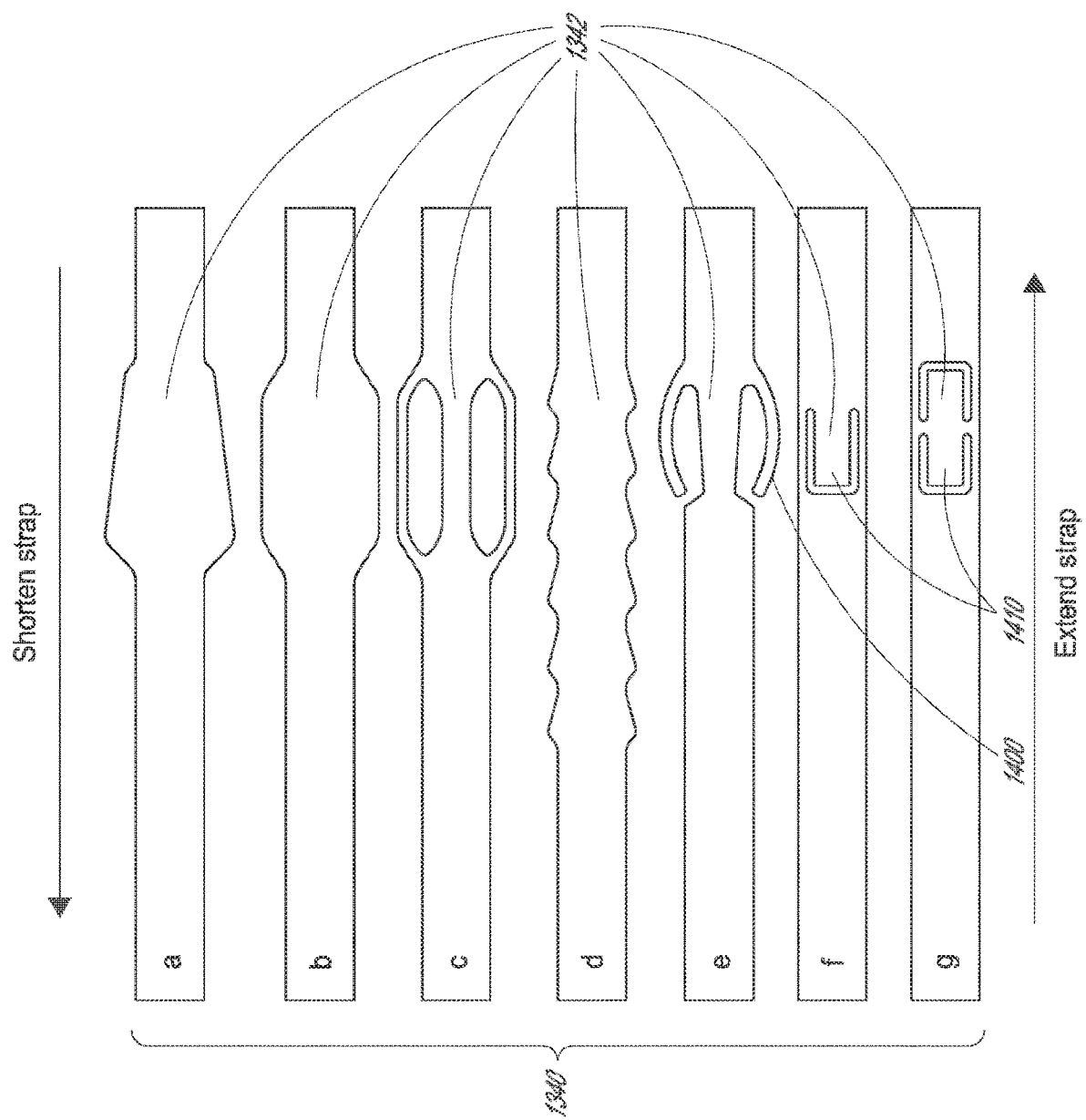
FIG. 14 is a front view of several embodiments of the lock of the headgear of FIGS. 13a and 13b.

FIG. 14 snows a variety of configurations that the lock 1342 may take. In some configurations, the ease with which the length of the strap 1310 can be adjusted is biased towards one direction. For instance, configurations 'a' and 'd' may make it easier to shorten the head-strap length than to extend it. The steeper increase in substrate width w at one end can increase the friction between the strap 1310 and the substrate 1340, thereby making it more difficult for the strap 1310 to pass over the substrate 1340 in one direction.

In various embodiments, the lock 1342 comprises one or more features, e.g., arms or tabs, configured to press against or catch on an inner portion of the strap 1310. For example, configuration 'e' comprises curved arms 1400 that extend from the width of the substrate 1340 and are open at one end. When the strap 1310 is pulled over the open end of the arms 1400 (to extend the strap length), the arms 1400 tend to deflect outward and the strap tends to press against or catch on the ends and extension of the strap length will be restricted. When the head-strap is pulled over the lock 1342 in the other direction, the curved arms 1400 deflect inwards at the open end, thereby reducing the width of the substrate 1340 and the associated friction. The inward deflection of the arms 1400, therefore, makes it easier to shorten the length of the strap 1310.

Configurations 'f' and 'g' include raised tabs 1410 that extend from the thickness of the substrate 1340. The tabs 1410 have a substantially rectangular profile, wherein three sides of the tab are detached from the substrate 1340. The connected side of the tabs 1410 forms a living hinge with the substrate 1340, such that the tabs 1410 flex in and out of alignment with the surface of the substrate 1340. The detached end will catch on the strap 1310 in a similar manner to the curved arms 1400 of configuration 'e' when the strap 1310 is pulled over the lock 1342 in a direction that moves from the detached end towards the hinged end of the tab 1410.

Figure 15:
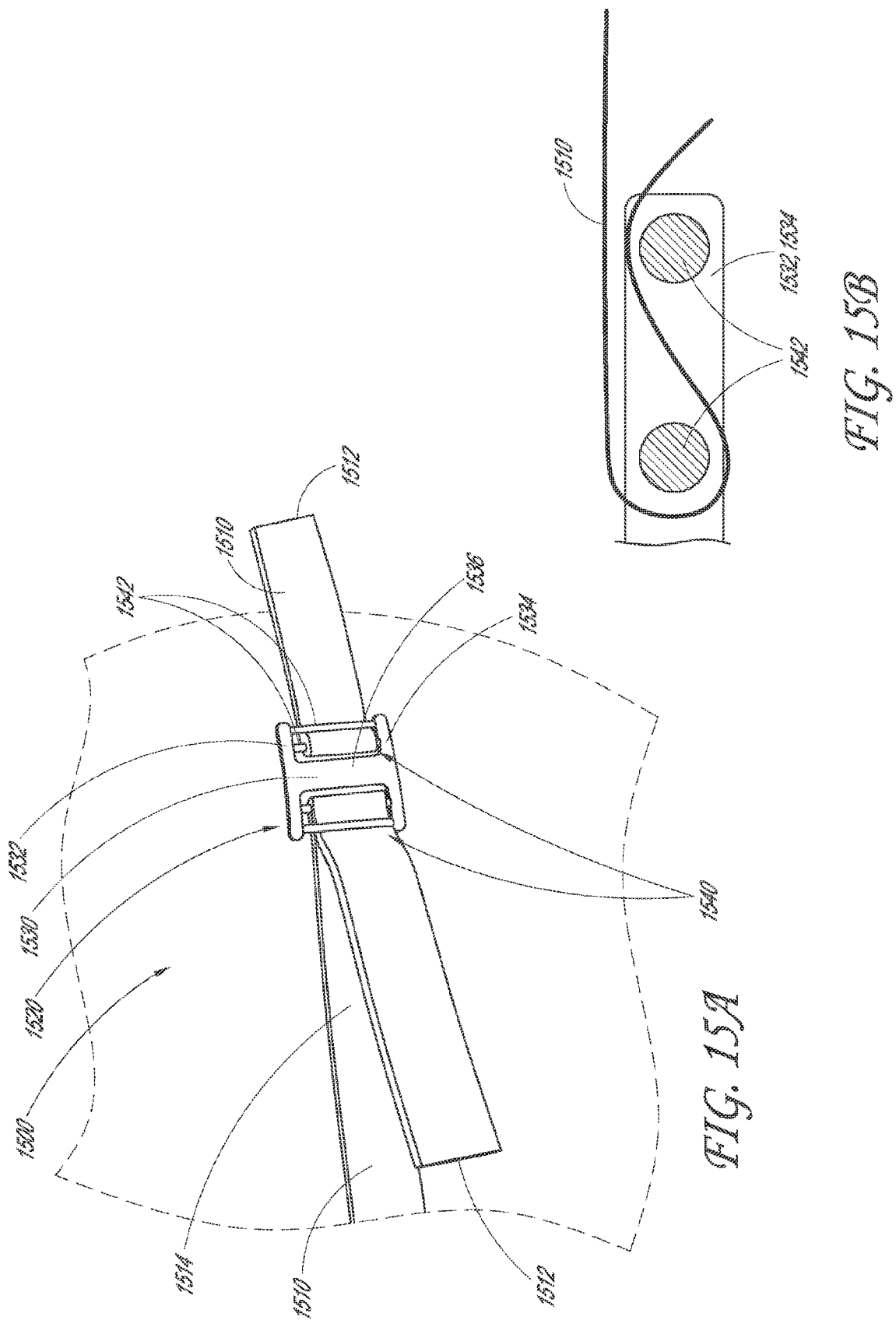

Rotating Post Buckle:

In certain embodiments, as shown in FIGS. 15a and 15b, a headgear 1500, e.g., for a respiratory mask, can include a pair of straps 1510 adjustably coupled to each other, and a buckle 1520. The buckle 1520 comprises a first end and a second end. The buckle 1520 comprises an adjustment mechanism 1540 at each of the first and second ends of the buckle 1520 to adjustably couple to a corresponding one of the pair of straps 1510. Each adjustment mechanism 1540 can comprise a pair of rotatable posts 1542. For example, FIG. 15a shows the rear portion of a headgear 1500 comprising first and second straps 1510 and a buckle 1520, wherein the first and second straps 1510 are adjustably connected by the buckle 1520 at the rear of a user's head (in use). The first and second straps 1510 are coupled to the mask or a mask connector on the other end of the straps 1510 (not shown). In some embodiments, the first and/or second straps 1510 comprise fabric. In addition, in some embodiments, the first and/or second strap 1510 can comprise elastic material. For example, the first and/or second straps 1510 can comprise a length of knitted elastic material, which may or may not be tubular.

In some embodiments, the buckle 1520 comprises a plastic body 1530. For example, the plastic body 1530 in some embodiments comprises a first or an upper arm 1532, a second or a lower arm 1534 and a stem 1536 that together form a substantially '1' shaped profile, and an adjustment mechanism 1540 located within each lateral side of the plastic body (e.g., one for each strap 1510). Each of the adjustment mechanisms 1540 can comprise a pair of posts 1542 that are offset from each other. In some embodiments, the posts 1542 are configured to extend perpendicularly between, and be rotatably coupled to, the upper arm 1532 and the lower arm 1534.

In various embodiments, the adjustment mechanisms 1540 are configured to allow the straps 1510 to be threaded around the posts 1542 in a torturous path that is substantially 's' shaped, as shown in FIG. 15b. This torturous path induces friction forces between the straps 1510 and the adjustment mechanisms 1540, such that the straps 1510 are retained at a user defined length. As a result of the straps 1510 being elastic in some embodiments, it can be difficult to draw them through a buckle with fixed posts. This is because the strap 1510 tends to stretch before the friction between the strap and the buckle is overcome. In certain embodiments, the adjustment mechanisms 1540 of the present disclosure utilize the rotatably coupled posts 1542 to address this problem by rotating under a lower applied force than is required for the straps to overcome the friction forces between components. In some other embodiments, the first and/or second straps 1510 can comprise inelastic material.

The length of the straps 1510 can be shortened and, thus, the size of the headgear 1500 reduced, by pulling the strap ends 1512 away from the buckle 1520. The length of the straps 1510 can be lengthened by pulling the head contacting portion 1514 of the straps away from the buckle 1520.

Figure 16:
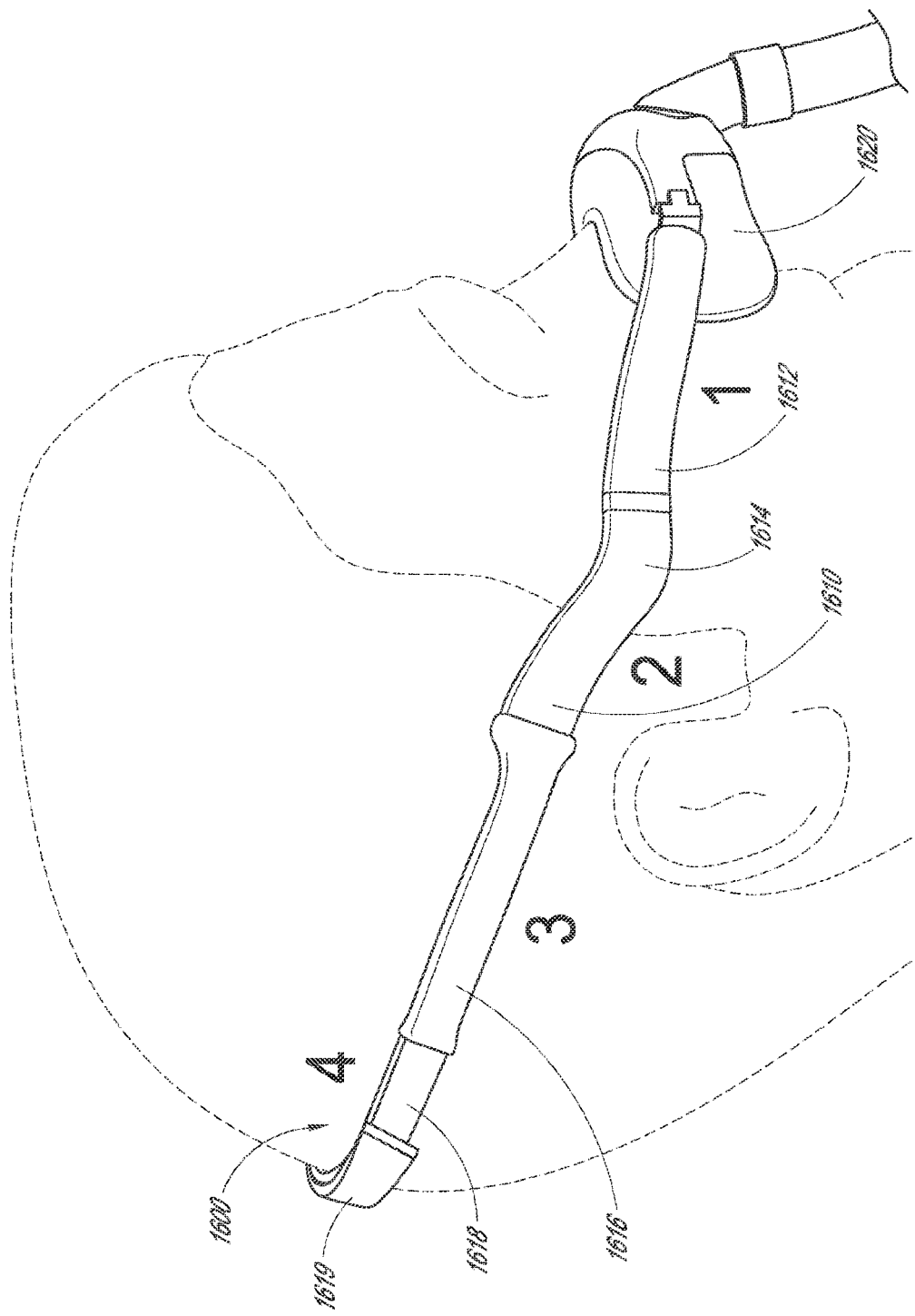
FIG. 16 is a side view of a fifth embodiment of the headgear of the present disclosure, worn by a user.

Single Strap Headgear with Variable Elasticity:

In certain embodiments, a headgear, e.g., for a respiratory mask, can include at least one side strap comprising a plurality of regions. Each region can differ from the other regions in at least one property. The property can include elasticity, flexibility, density, and/or geometry. As an example, FIG. 16 shows headgear 1600 comprising two side straps 1610 (only one is visible) that are configured to be adjustably attached to each other by a connector such as a buckle (not shown) at one end (e.g., at the rear of a user's head) and that connect to a mask frame 1620 at the other end. The side straps 1610 comprise first, second, third and fourth regions, 1612, 1614, 1616, 1618, which differ from each other in at least one physical attribute. The four regions 1612, 1614, 1616, 1618 are elongate and configured to be connected to each other in series (e.g., end on end). The four regions 1612, 1614, 1616, 1618 may be connected together by any suitable process, including, but not limited to, sewing or welding.

The first region 1612 is configured to connect with the mask frame 1620 at one end and to extend over the user's cheek (in use) to a second end that is proximal to the user's temple. In some embodiments, it comprises a laminated material such as neoprene or Breath-o-Prene™, having at least one layer of relatively high density foam. The first region 1612 is substantially inelastic and configured to provide a substantially stable connection to the mask: frame 1620 via a hook, clip or other suitable connecting component. The first region 1612 can be a substantially straight region. The geometry of this section (i.e., the thickness and the width) in combination with the material used will provide more flexibility in one direction than in others. There will be greater flexibility in a direction that is substantially normal to a user's face (in use) than there is in a vertical direction (when a user is sitting in an upright position). Flexibility that is normal to the user's face may help the headgear 1600 to conform to the facial geometry of each individual user. The restricted vertical flexibility can help to minimize vertical rolling movement of the respiratory mask on a user's face.

In various embodiments, the second region 1614 is made from a material that is substantially the same as the first region 1612 and provides similar stability. It comprises a 'dog leg' or 's' shaped profile having an angle or curvature which allows the side strap 1610 to sit below the user's eyes and above their ears, such that the user's peripheral vision is not significantly obstructed and such that no force is applied to the user's ears, each of which may be beneficial for user comfort. For example, the profile of the second region 1614 can include an angle or curve above and forward of the user's ear. The density of the chosen material is such that forces applied through the headgear 1600, during use, do not deform the dog-leg shape and cause the side strap 1610 to conic into contact with the user's ears or get too close to their eyes. In an alternative embodiment, the first and second regions 1612 and 1614 can be formed as a single component.

The third region 1616 of the side strap 1610 can be substantially elastic. For example, in some embodiments, the third region 1616 of the side strap 1610 comprises a length of elastic. In some embodiments, the length of elastic may be circular knitted elastic. This substantially elastic section is configured to allow the headgear 1600 to be stretched over a user's head to make donning and doffing the respiratory mask quick and easy.

In some embodiments, the fourth region 1618 comprises an elongate section of a laminated material, such as a material comprising neoprene or Breath-o-Prene™, that has a relatively lower density than the material of the first and second regions 1612, 1614. This provides sufficient flexibility in some embodiments to allow the fourth region 1618 to pass through a buckle and double back on itself to form a length adjustment means for the headgear. The fourth region also comprises a length securing tab 1619 at the end that is not connected to the third region 1616. In some embodiments, the length securing tab 1619 comprises the hook component of a 'hook and loop' fastening system, such as Velcro™. It can be configured to connect to a loop component that is formed by a fabric layer of the laminated material of the fourth region 1618. The fourth region 1618 is substantially inelastic, which enables it to slide freely through buckle (not shown without stretching when the length securing tabs are pulled on.

Alternative embodiments of the headgear 1600 may comprise different curved shapes to pass between a user's eyes and ears. The number of differing regions may vary between embodiments. For instance, one embodiment may not include an elastic region and may rely on a more elastic laminated material (e.g., Breath-o-Prene™) region to aide in donning and doffing of the mask. In yet another embodiment, the fourth region 1618 may be replaced by an extended elastic third section 1616.

Single Strap with Resilient Core

FIG. 17 shows an embodiment wherein a headgear 1700 comprises a single tubular strap 1710 and a resilient core (not visible). The strap 1710 comprises a first strap end, a second strap end, and a length therebetween. The resilient core comprises a first core end and a second core end In some embodiments, the strap 1710 comprises a fabric. The strap 1710 can comprise elastic or inelastic material. As one example, the strap 1710 comprises a knitted elastic strap. In some embodiments, each of the first strap end and the second strap end extends respectively beyond the first core end and the second core end of the resilient core. Each of the first strap end and the second strap end can pass through a corresponding connector configured to couple the headgear to a mask. For example, in some embodiments, the strap 1710 is tubular and is configured to encase and conform to the shape of the resilient core. The strap ends 1712 may be open or sealed (once threaded over the resilient core) and are configured to be passed through a connector 1720. As shown in FIG. 17, the connector 1720 comprises a hook 1722, which is configured to connect to a mask frame 1730, and a loop 1724, through which the strap 1710 is configured to pass. The length of the strap 1710 is configured to be adjusted by moving the strap end 1712 through the loop 1724.

In some embodiments, the resilient core is configured to extend around the back of a user's head from one cheek to the other, passing between the eyes and ears. In some embodiments, the resilient core comprises a moulded plastic. The resilient core can be made from a resilient but flexible material, such as, but not limited to, nylon or polypropylene, which allows the resilient core to substantially maintain its moulded shape during use. The resilient core is relatively flexible in a direction that is substantially normal to the user's head (when the mask is in use), such that the headgear 1700 may somewhat conform to the user's head. The material selection and width of the resilient core minimizes the flexibility of the headgear in a vertical direction (in use, with a user sitting in an upright position), which may provide the headgear 1700 with stability on the user's head.

The resilient core can comprise a three-dimensional structure that passes below a user's eyes and above a user's ears to avoid discomfort of the strap 1710 being too close to the user's eyes or applying pressure to the top of the user's ears. For example, in some embodiments, the resilient core comprises a 'dog leg' or 's' shaped profile, e.g., having an angle or curvature, that is configured to generally avoid the user's eyes and ears. The resilient core can also be configured to extend forward of a user's ears and rearward of the mask. For example, in some embodiments, the resilient core is further configured such that it does not extend through the entire length of the strap 1710. There is a gap between the ends of the resilient core and where the strap 1710 passes through the loop 1712 of the connectors 1720. This gap provides a section in the strap 1710 that is capable of stretching during donning and doffing of the headgear 1700 and the attached respiratory mask. The gap also provides a flexible section near strap ends 1712 that is threaded through die connector 1720 and doubled back on itself in order to adjust the length of the strap 1720 and, thus, the overall headgear size. Once the headgear 1700 has been adjusted to the user's desired size, the strap ends 1712 are secured in place by any suitable fixing means, such as, but not limited to, mechanical clips or Velcro™ tabs.

As used herein, the term respiratory mask refers to any sealing or non-sealing mask or patient interface that may be used to deliver respiratory therapy to the airways of a patient. Respiratory masks and/or respiratory interfaces include, but are not limited to, full face masks configured to seal about the nose and mouth of a patient, nasal masks that seal around or under a patient's nose, direct nasal masks or interfaces that include prongs or pillows that seal about a patient's nares, or non-sealing interfaces such as but not limited to nasal cannula.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features. For example, various embodiments of a headgear are disclosed herein with features such as one or more straps and connectors. It is understood that one or more features from one embodiment can be used with one or more features from other embodiments. Also, in embodiments that utilize a plurality of a certain feature, e.g., a plurality of straps or a plurality of connectors, it is understood that the plurality can be the same or different from each other. Furthermore, the material, shape, size, color, and/or other physical properties of certain features (e.g., straps, connectors) can be based on the intended mask, user, and/or expected force to counteract.

Recitation of ranges herein is merely intended to serve as shorthand method of referring individually to each separate sub-range or value falling within the range, unless otherwise indicated herein, and each separate sub-range or value is incorporated into the specification as if it were individually recited herein.

Reference to any prior art in this specification is not, and should not be taken as, an acknowledgement or any form of suggestion that that prior art forms part of the common general knowledge in the field of endeavor in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A headgear for a respiratory mask, the headgear comprising:
a first strap;
a second strap;
a pair of buckles comprising a corresponding buckle for the first and second straps, each corresponding buckle comprising:
a glider portion;
a strap attachment portion; and
a pivot connection between the glider portion and the strap attachment portion,
wherein the glider portion has a first side in contact with the strap attachment portion, and a second side facing away from the strap attachment portion, the first side of the glider portion opposite the second side,
wherein the strap attachment portion has a first side in contact with the glider portion, and a second side facing away from the glider portion, the first side of the strap attachment portion opposite the second side,
wherein each of the first and second straps comprises a first end, a second end, and a length therebetween,
wherein each of the first and second straps is configured to connect to the respiratory mask at the first end, to adjustably couple to the corresponding buckle at the glider portion, and to be fixedly coupled to the strap attachment portion of another buckle of the pair of buckles at the second end,
wherein each buckle is configured to move along the length of the first or second strap to adjust the size of the headgear,
wherein the pivot connection comprises a snap-fit dome and a ring,
wherein the snap-fit dome is configured to engage with and be received by the ring such that the ring can rotate about the snap-fit dome,
wherein the first side of the glider portion comprises the ring such that the entirety of the ring and the glider portion form a first single piece, and
wherein the first side of the strap attachment portion comprises the snap-fit dome such that the entirety of the snap-fit dome and the strap attachment portion form a second single piece.

2. The headgear of claim 1, wherein the first or second strap comprises a tubular structure.

3. The headgear of claim 1, wherein for at least one buckle, the glider portion includes at least one aperture through which the first or second strap passes.

4. The headgear of claim 1, wherein for at least one buckle, the glider portion and the strap attachment portion comprise a semi-circular profile on one end and a rectangular profile on another end, and wherein for the at least one buckle, the pivot connection is located at the semi-circular profile ends of the glider portion and the strap attachment portion, and wherein the semi-circular profile ends overlap.

5. The headgear of claim 1, wherein at least one of the first and second straps is overmoulded to the strap attachment portion of the other buckle or wherein at least one of the first and second straps is welded to the strap attachment portion of the other buckle.

6. The headgear of claim 1, wherein the headgear is configured to be adapted between a first configuration and a second configuration, wherein the first configuration comprises portions of the first and second straps overlapping in a region between the pair of buckles; and
wherein the second configuration comprises the portions of the first and second straps bifurcating in the region between the pair of buckles and wherein the pair of buckles is configured to adjust the size of the headgear while in the second configuration.

7. A respiratory mask assembly, comprising:
a respiratory mask;
a headgear comprising a first strap, a second strap, and a pair of buckles comprising a corresponding buckle for the first and second straps, each corresponding buckle comprising:
a glider portion;
a strap attachment portion; and
a pivot connection between the glider portion and the strap attachment portion,
wherein the glider portion has a first side in contact with the strap attachment portion, and a second side facing away from the strap attachment portion, the first side of the glider portion opposite the second side,
wherein the strap attachment portion has a first side in contact with the glider portion, and a second side facing away from the glider portion, the first side of the strap attachment portion opposite the second side,
wherein the pivot connection comprises a snap-fit dome and a ring,
wherein the snap-fit dome is configured to engage with and be received by the ring such that the ring can rotate about the snap-fit dome,
wherein the first side of the glider portion comprises the ring such that the entirety of the ring and the glider portion form a first single piece,
wherein the first side of the strap attachment portion comprises the snap-fit dome such that the entirety of the snap-fit dome and the strap attachment portion form a second single piece,
wherein each of the first and second straps comprises a first end, a second end, and a length therebetween, wherein each of the first and second straps is connectable to the respiratory mask at the first end, is adjustably coupled to the corresponding buckle at the glider portion, and is fixedly coupled to the strap attachment portion of another buckle of the pair of buckles at the second end;
wherein each buckle is configured to move along the length of the first or second strap to adjust the size of the headgear; and
wherein the headgear is configured to be adapted between a first configuration and a second configuration, wherein the first configuration comprises portions of the first and second straps overlapping in a region between the pair of buckles and wherein the second configuration comprises the portions of the first and second straps bifurcating in the region between the pair of buckles and wherein the pair of buckles is configured to adjust the size of the headgear while in the second configuration.

8. The respiratory mask assembly of claim 7, wherein the first or second strap comprises a tubular structure.

9. The respiratory mask assembly of claim 7, wherein for at least one buckle, the glider portion includes at least one aperture through which the first or second strap passes.

10. The respiratory mask assembly of claim 7, wherein for at least one buckle, the glider portion and the strap attachment portion comprise a semi-circular profile on one end and a rectangular profile on another end, and wherein for the at least one buckle, the pivot connection is located at the semi-circular profile ends of the glider portion and the strap attachment portion, and wherein the semi-circular profile ends overlap.

11. The respiratory mask assembly of claim 7, wherein at least one of the first and second straps is overmoulded to the strap attachment portion of the other buckle or wherein at least one of the first and second straps is welded to the strap attachment portion of the other buckle.

12. The headgear of claim 1, wherein the pivot connection is configured to impinge upon, and apply a friction force to, the first strap or the second strap.

13. The headgear of claim 1, wherein the pivot connection is configured to couple the glider portion and the strap attachment portion in a direction along an axis of rotation of the pivot connection.

14. The respiratory mask assembly of claim 7, wherein the pivot connection is configured to impinge upon, and apply a friction force to, the first strap or the second strap.

15. The respiratory mask assembly of claim 7, wherein the pivot connection is configured to couple the glider portion and the strap attachment portion in a direction along an axis of rotation of the pivot connection.

16. The headgear of claim 1, wherein the pivot connection comprises only two components, the two components comprising the snap-fit dome and the ring.

17. The headgear of claim 1, wherein the ring defines a continuous inner surface, wherein the snap-fit dome defines a completely annular surface that only engages with the continuous inner surface of the ring.

18. The respiratory mask assembly of claim 7, wherein the pivot connection comprises only two components, the two components comprising the snap-fit dome and the ring.

19. The respiratory mask assembly of claim 7, wherein the ring defines a continuous inner surface, wherein the snap-fit dome defines a completely annular surface that only engages with the continuous inner surface of the ring.

* * * * *